US008246624B2

(12) United States Patent
Forton et al.

(10) Patent No.: US 8,246,624 B2
(45) Date of Patent: Aug. 21, 2012

(54) SPINAL ROD INSERTION TOOL AND METHOD

(75) Inventors: Charles R. Forton, Leander, TX (US); Peter Thomas Miller, Austin, TX (US)

(73) Assignee: Zimmer Spine, Inc., Minneapolis, MN (US)

( * ) Notice: Subject to any disclaimer, the term of this patent is extended or adjusted under 35 U.S.C. 154(b) by 342 days.

(21) Appl. No.: 12/507,961

(22) Filed: Jul. 23, 2009

(65) Prior Publication Data
US 2011/0022088 A1 Jan. 27, 2011

(51) Int. Cl.
*A61B 17/70* (2006.01)
*A61B 17/88* (2006.01)

(52) U.S. Cl. ........................ 606/86 A; 606/246; 606/279
(58) Field of Classification Search .......... 606/246–279, 606/86 A
See application file for complete search history.

(56) References Cited

U.S. PATENT DOCUMENTS

| | | | |
|---|---|---|---|
| 6,146,386 A | 11/2000 | Blackman et al. |
| 6,530,929 B1 | 3/2003 | Justis et al. |
| 7,008,422 B2 | 3/2006 | Foley et al. |
| 7,011,660 B2 | 3/2006 | Sherman et al. |
| 7,188,626 B2 | 3/2007 | Foley et al. |
| 7,371,239 B2 | 5/2008 | Dec et al. |
| 7,396,360 B2 | 7/2008 | Lieberman |
| 7,520,879 B2 | 4/2009 | Justis et al. |
| 2003/0208203 A1 | 11/2003 | Lim et al. |
| 2005/0038432 A1 | 2/2005 | Shaolian et al. |
| 2005/0131419 A1* | 6/2005 | McCord et al. ................. 606/99 |
| 2005/0154389 A1 | 7/2005 | Selover et al. |
| 2005/0171540 A1 | 8/2005 | Lim et al. |
| 2005/0192589 A1 | 9/2005 | Raymond et al. |
| 2005/0277934 A1 | 12/2005 | Vardiman |
| 2006/0036244 A1 | 2/2006 | Spitler et al. |
| 2006/0247630 A1 | 11/2006 | Iott et al. |
| 2007/0016194 A1 | 1/2007 | Shaolian et al. |
| 2007/0078460 A1 | 4/2007 | Frigg et al. |
| 2008/0051781 A1 | 2/2008 | Geist et al. |
| 2008/0077138 A1 | 3/2008 | Cohen et al. |
| 2008/0312703 A1 | 12/2008 | Hestad et al. |
| 2009/0105774 A1 | 4/2009 | Jones et al. |
| 2009/0171391 A1 | 7/2009 | Hutton et al. |

OTHER PUBLICATIONS

European Extended Search Report (ESR) for European Application No. 10 007 573.8, mailed Sep. 21, 2010, 8 pgs.

* cited by examiner

*Primary Examiner* — Eduardo C Robert
*Assistant Examiner* — Nicholas Plionis
(74) *Attorney, Agent, or Firm* — Seager Tufte & Wickhem LLC

(57) ABSTRACT

Embodiments described herein provide systems and methods for inserting a spinal stabilization rod. A rod insertion tool can include a body defining a passage, a pivot rod disposed in the passage and a rod retaining member. Movement of the pivot rod can cause the rod retaining member to rotate and consequently the spinal stabilization rod to rotate. The rod insertion tool can be sized to fit through channels in sleeves used during implantation of a spinal stabilization system.

20 Claims, 25 Drawing Sheets

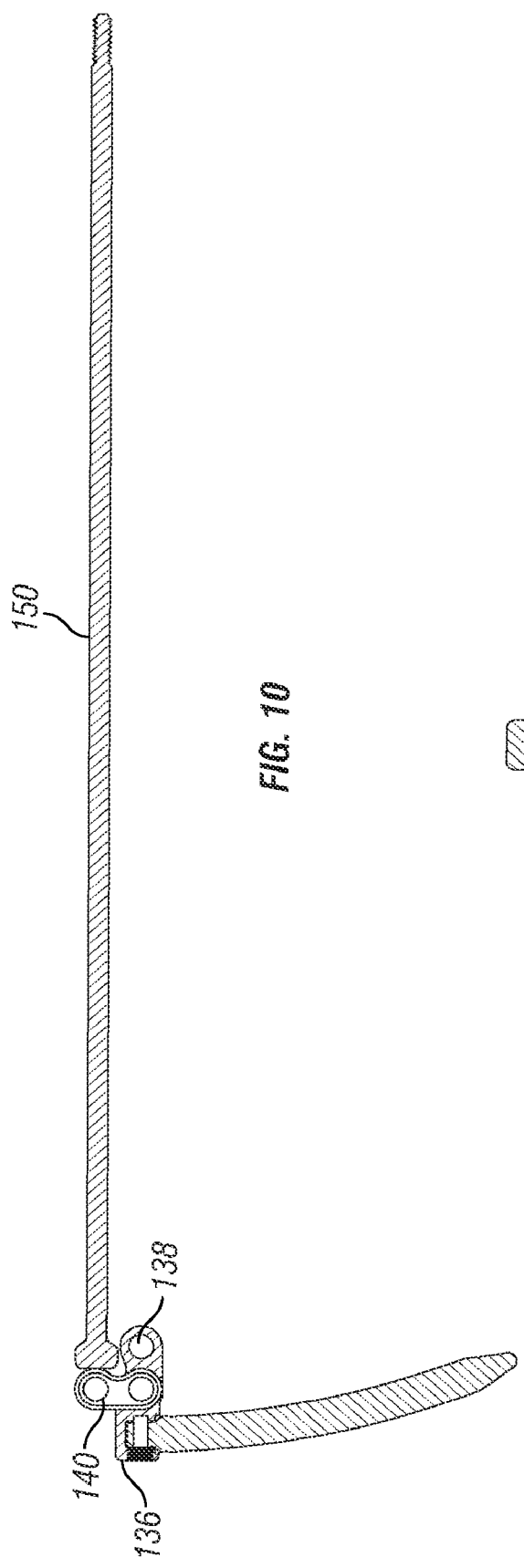
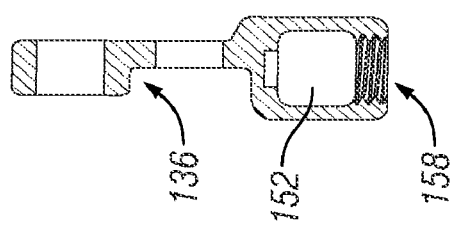
FIG. 10
FIG. 11

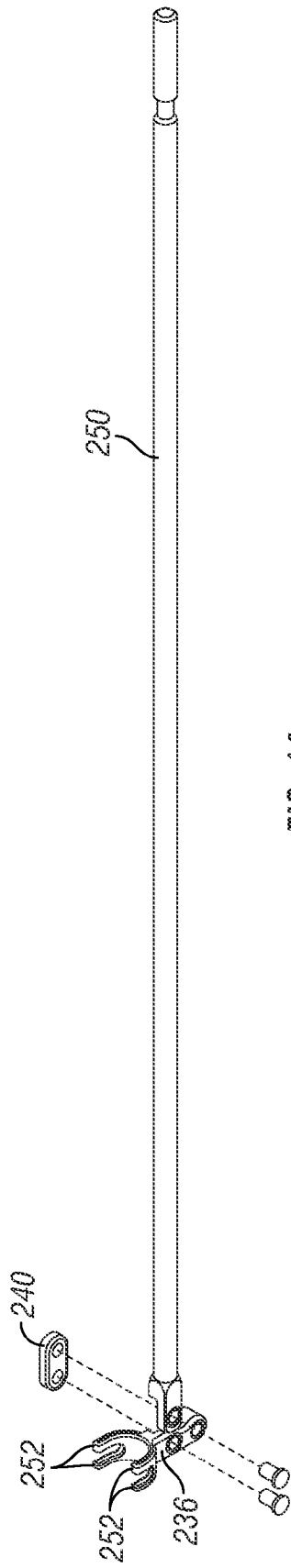

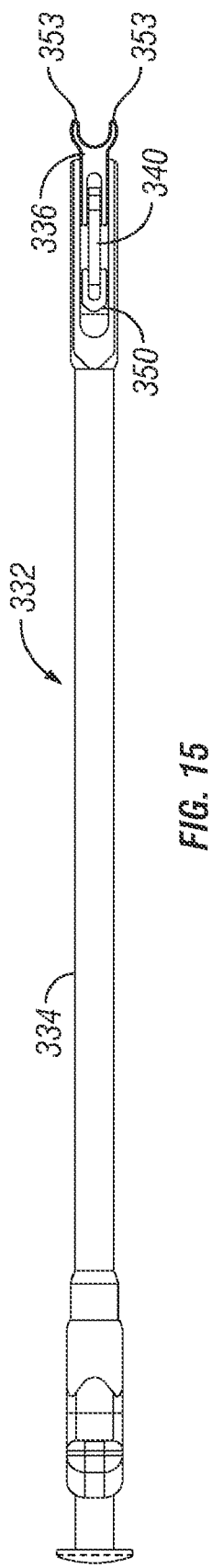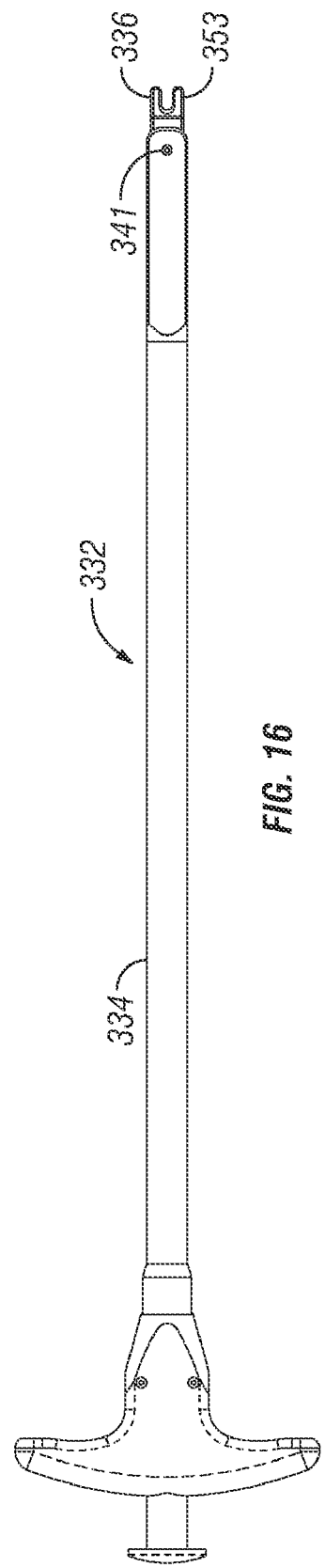

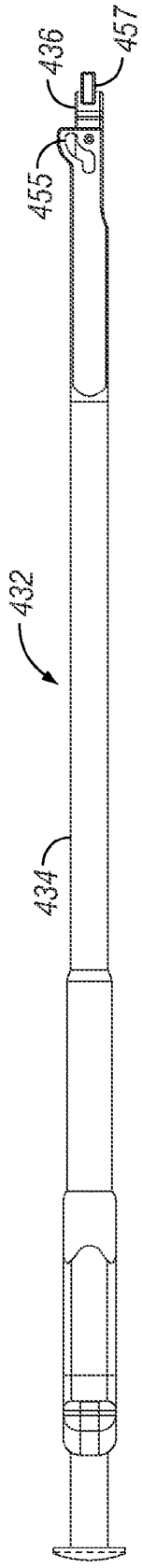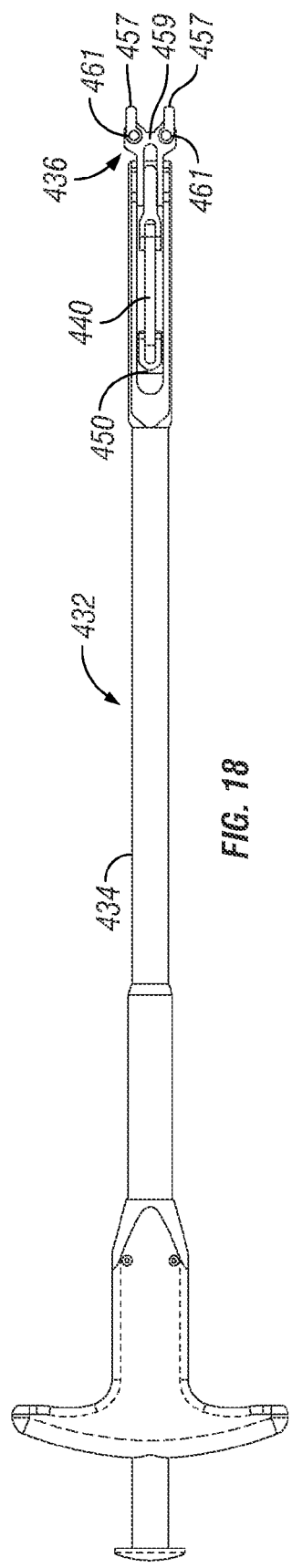

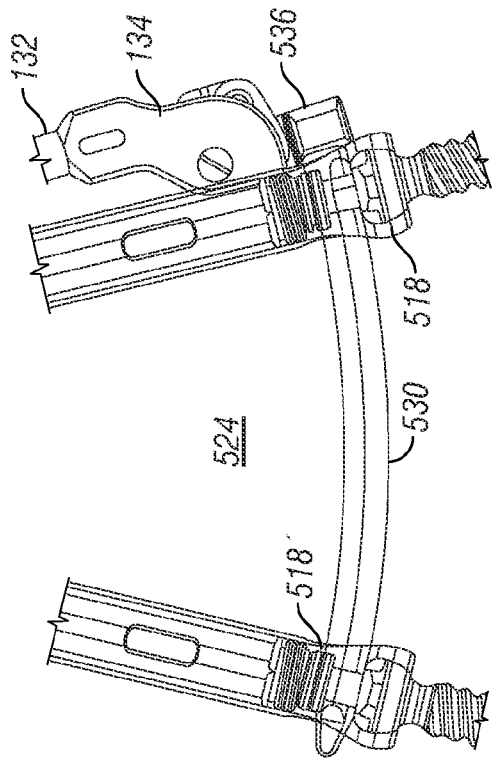
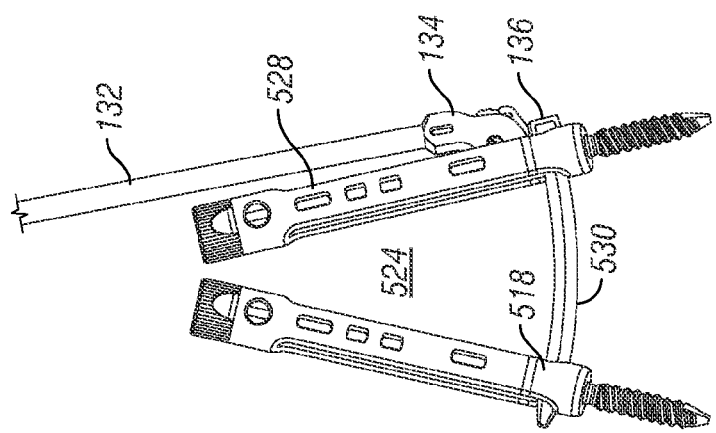
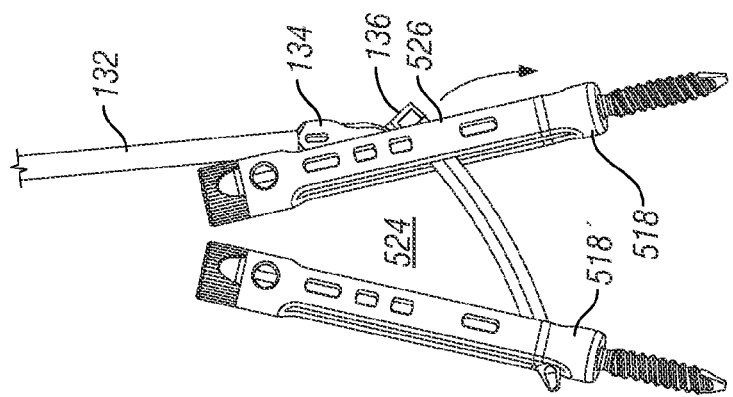

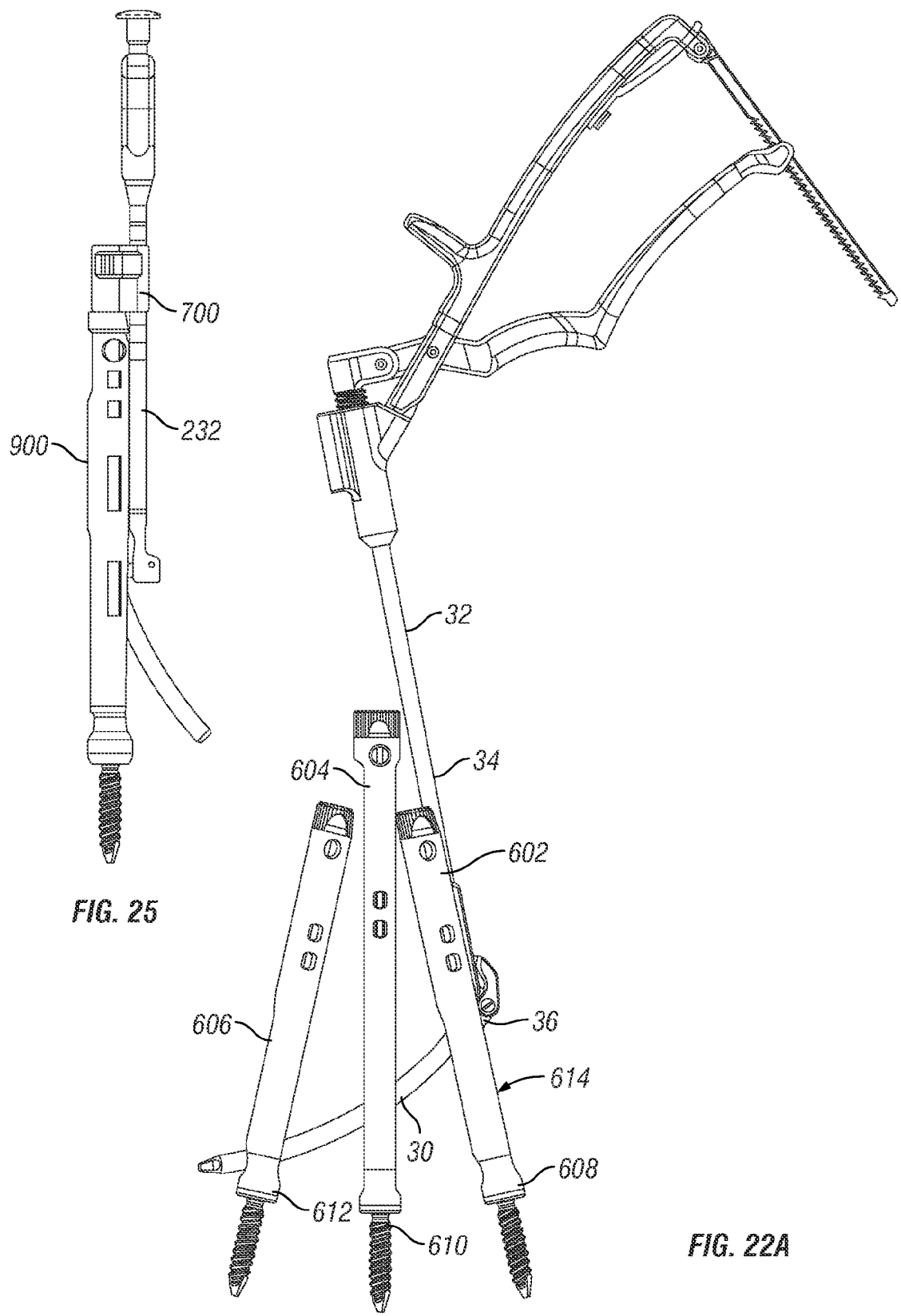

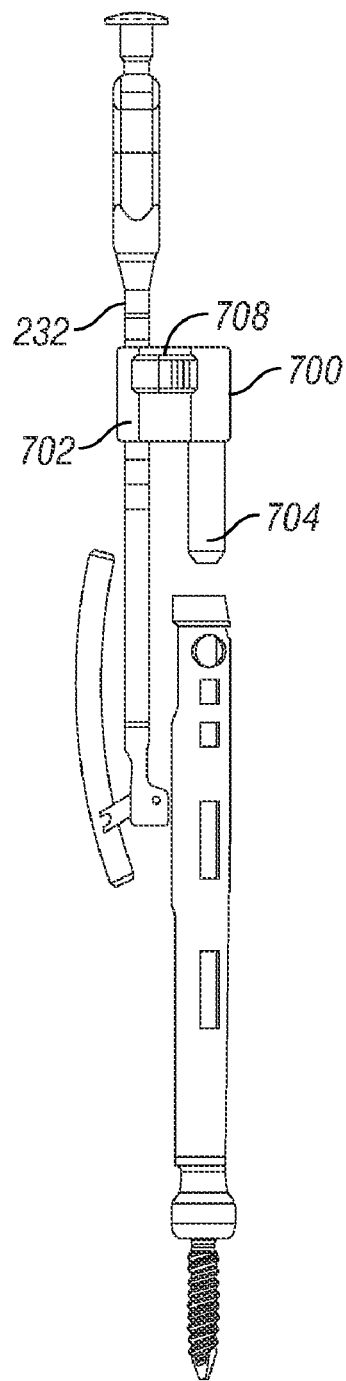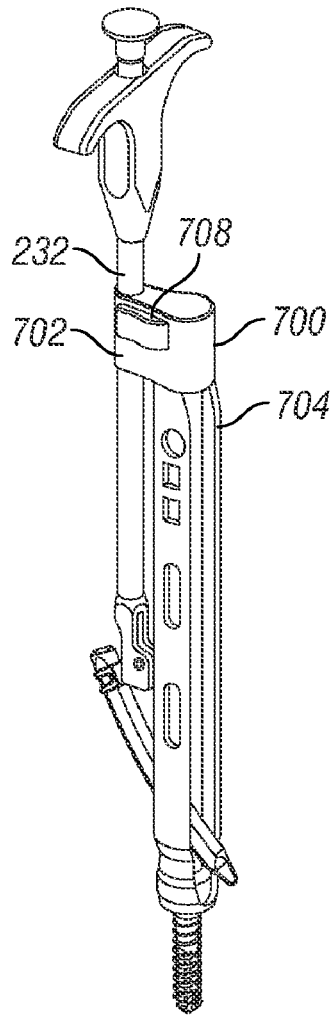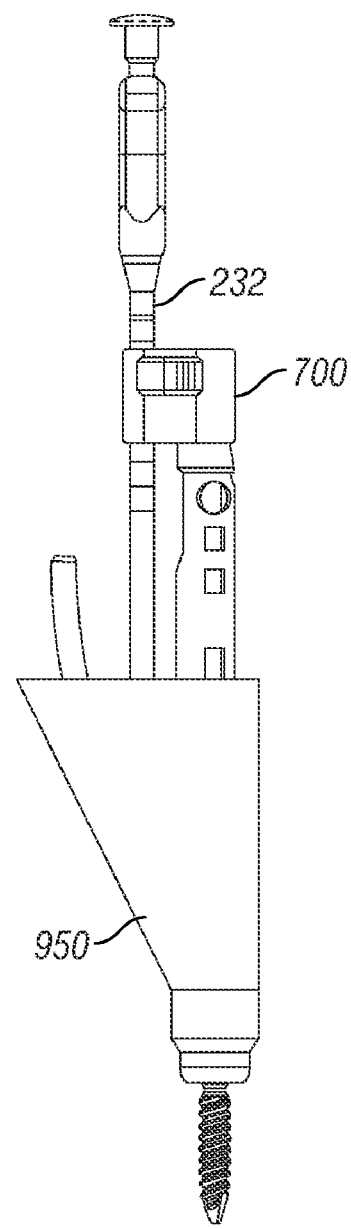
*FIG. 23A*  *FIG. 23B*  *FIG. 26*

SPINAL ROD INSERTION TOOL AND METHOD

TECHNICAL FIELD

The disclosure describes spinal stabilization systems and methods including systems and methods for inserting spinal stabilization rods percutaneously.

BACKGROUND

Bone may be subject to degeneration caused by trauma, disease, and/or aging. Degeneration may destabilize bone and affect surrounding structures. For example, destabilization of a spine may result in alteration of a natural spacing between adjacent vertebrae. Alteration of a natural spacing between adjacent vertebrae may subject nerves that pass between vertebral bodies to pressure. Pressure applied to the nerves may cause pain and/or nerve damage. Maintaining the natural spacing between vertebrae may reduce pressure applied to nerves that pass between vertebral bodies. A spinal stabilization procedure may be used to maintain the natural spacing between vertebrae and promote spinal stability.

Spinal stabilization may involve accessing a portion of the spine through soft tissue. Conventional stabilization systems may require a large incision and/or multiple incisions in the soft tissue to provide access to a portion of the spine to be stabilized. Conventional procedures may result in trauma to the soft tissue, for example, due to muscle stripping.

United States Patent Publication No. 2008/0051781 and U.S. Pat. No. 7,011,660 show systems to insert a rod that uses a sextant like device to guide a rod to a surgical site. However, these systems require that an additional incision be made some distance from the surgical site leading to an additional area that must heal. In addition, the spinal stabilization rod must tunnel through tissue for an extended distance before reaching the surgical site.

SUMMARY

Embodiments and various features and advantageous details thereof are explained more fully with reference to the exemplary, and therefore non-limiting, embodiments illustrated in the accompanying drawings and detailed in the following description. Descriptions of known starting materials and processes may be omitted so as not to unnecessarily obscure the disclosure in detail. It should be understood, however, that the detailed description and the specific examples, while indicating the particular embodiments, are given by way of illustration only and not by way of limitation. Various substitutions, modifications, additions and/or rearrangements within the spirit and/or scope of the underlying inventive concept will become apparent to those skilled in the art from this disclosure.

Embodiments described herein provide systems and methods for inserting a spinal stabilization rod. One embodiment can comprise a rod insertion tool comprising an outer body defining a passage, a pivot shaft translatable in the passage of the outer body, a rod retaining member rotatable relative the outer body and a linkage coupled to the rod retaining member and the pivot rod so that the rod retaining member rotates about the axis of rotation when the pivot rod translates relative to the outer body. According to one embodiment, the rod insertion tool can be sized so that the insertion tool can fit in a channel in the wall of a sleeve used to implant the spinal stabilization system.

Another embodiment includes a method of inserting a spinal stabilization rod that comprises coupling the spinal stabilization rod to a rod retaining member of a rod insertion tool, providing a first sleeve coupled to a first bone fastener and a second sleeve coupled to a second bone fastener, inserting the spinal stabilization rod into the human body through an incision using the insertion tool, moving the spinal stabilization rod into the human body using the rod insertion tool with at least a portion of the rod insertion tool passing through a channel in a side of the first sleeve during the moving, and moving a pivot rod internal to a body of the rod insertion tool to cause the rod retaining member to rotate relative to the rod insertion tool body to position the rod in a second orientation spanning the first and second bone fasteners. The method can further include releasing the spinal stabilization rod from the rod retaining member after the spinal stabilization rod is secured to at least one of the bone fasteners.

Yet another embodiment includes a method for inserting a spinal stabilization rod comprising, coupling a spinal stabilization rod retaining member of a rod insertion tool, and implanting the spinal stabilization rod into a patient percutaneously using the rod insertion tool to rotate the spinal stabilization rod from a first orientation with a reduced profile to a second orientation. According to one embodiment, the rod insertion tool comprises a body having a passage, a rod retaining member coupled to the body and rotatable relative to the body, a pivot rod disposed in the passage and a linkage coupled to the pivot rod and the rod retaining member. Movement of the pivot rod causes the rod retaining member to rotate relative to the body.

BRIEF DESCRIPTION OF THE DRAWINGS

A more complete understanding of the embodiments and the advantages thereof may be acquired by referring to the following description, taken in conjunction with the accompanying drawings in which like reference numbers indicate like features and wherein:

FIG. 10 is a diagrammatic representation of a portion of an embodiment of a rod insertion tool;

FIG. 11 is a diagrammatic representation of an embodiment of a rod retaining member;

FIG. 14 is a diagrammatic representation of a portion of the rod insertion tool of FIG. 12;

FIGS. 15 and 16 are diagrammatic representations of another embodiment of a rod insertion tool;

FIGS. 17 and 18 are diagrammatic representations of yet another embodiment of a rod insertion tool;

FIGS. 20A-20C are diagrammatic representations of inserting a trial rod;

FIGS. 22A-22G are diagrammatic representations of inserting a rod for a multi-level stabilization procedure;

FIGS. 23A-23B are diagrammatic representations of another embodiment of a rod insertion tool and adapter;

FIG. 25 is a diagrammatic representation of inserting a rod from an inner side of a sleeve;

FIG. 26 is a diagrammatic representation of using a dilator in conjunction with a rod insertion tool;

DETAILED DESCRIPTION

Figure 1:
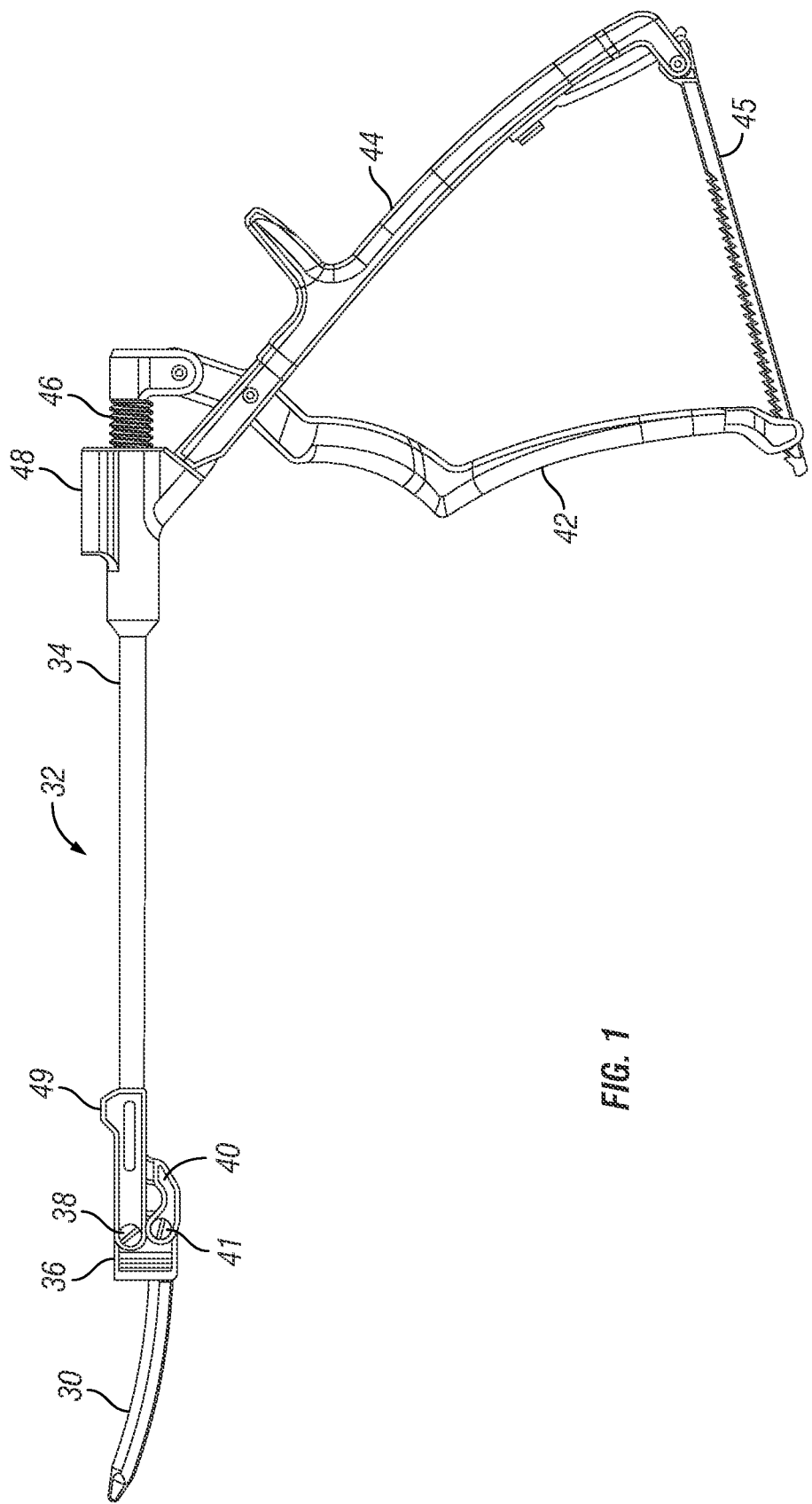
FIG. 1 is a diagrammatic representation of one embodiment of a rod and a rod inserter tool.

As used herein, the terms "comprises," "comprising," "includes," "including," "has," "having" or any other variation thereof, are intended to cover a non-exclusive inclusion. For example, a process, product, article, or apparatus that comprises a list of elements is not necessarily limited to only those elements but may include other elements not expressly listed or inherent to such process, process, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of, any term or terms with which they are utilized. Instead these examples or illustrations are to be regarded as being described with respect to one particular embodiment and as illustrative only. Those of ordinary skill in the art will appreciate that any term or terms with which these examples or illustrations are utilized encompass other embodiments as well as implementations and adaptations thereof which may or may not be given therewith or elsewhere in the specification and all such embodiments are intended to be included within the scope of that term or terms. Language designating such non-limiting examples and illustrations includes, but is not limited to: "for example," "for instance," "e.g.," "in one embodiment," and the like. Reference is now made in detail to the exemplary embodiments of the disclosure, examples of which are illustrated in the accompanying drawings. Wherever possible, like numerals will be used throughout the drawings to refer to like and corresponding parts (elements) of the various drawings.

A spinal stabilization can be inserted using open or minimally invasive techniques. In minimally invasive procedures, a small opening may need to be made in a patient. For example, for a single-level stabilization procedure on one side of the spine, the surgical procedure may be performed through a 2 cm to 4 cm incision formed in the skin of the patient. In some embodiments, the incision may be above and substantially between the vertebrae to be stabilized or in another location. In other embodiments, the incision may be above and substantially halfway between the vertebrae to be stabilized. In still other embodiments, multiple incisions can be made to allow tools to reach a surgical site. Dilators, a targeting needle, and/or a tissue wedge may be used to provide access to the vertebrae to be stabilized without the need to form an incision with a scalpel through muscle and other tissue between the vertebrae to be stabilized. A minimally invasive procedure may reduce an amount of post-operative pain felt by a patient as compared to invasive spinal stabilization procedures and reduce recovery time for the patient as compared to invasive spinal procedures.

Embodiments described in this disclosure provide systems and methods for inserting a spinal stabilization rod. In particular, embodiments of a rod insertion tool can be used for inserting a rod during a minimally invasive surgical technique without or reducing the need to extend incisions and without the need for additional incisions. The insertion tool can include a rod retaining member that is rotatable so that the rod can be held in various orientations during the insertion procedure. The rod retaining member can be coupled to a tool body in a manner that allows the rod retaining member to pivot about an axis. A pivot shaft can run through the body and be coupled to the rod retaining member so that movement of the inner shaft can cause the rod retaining member to rotate. The rod retaining member can be sized to minimize additional incisions and distraction of soft tissue by, for example, being sized to fit in a channel of a detachable sleeve coupled to the bone fastener that will secure the stabilization rod in the body.

FIG. 1 is a diagrammatic representation of a rod 30 and rod insertion tool 32. Insertion tool 32 can include an outer body 34 that defines a passage for a pivot rod. A rod retaining member 36 is coupled to outer body 34 in a manner that allows rod retaining member 36 to rotate relative to outer body 34 from a first position to a second position through a range of angles. According to one embodiment, a pin 38 can run through outer body 34 and rod retaining member 36 to create an axis of rotation for rod retaining member 36. A pivot rod 50 (shown in FIG. 2) can couple to rod retaining member 36 in a manner such that movement of the pivot rod in body 34 causes rod retaining member 36 to rotate about the axis of rotation. According to one embodiment, pivot rod 50 can couple to rod retaining member 36 through a linkage 40.

A handle 42 can connect to the pivot rod such that movement of the handle causes the pivot rod to translate in body 34. In the example of FIG. 1, handle 42 and handle 44 are in a Kerrison style arrangement such that squeezing handle 42 relative to handle 44 will cause the pivot rod to move forward. While a particular arrangement is shown for moving the pivot rod relative to body 34, any suitable mechanism can be used. A biasing member 46 can be used to maintain the pivot rod in a particular position when a user does not squeeze handle 42. The biasing member, in this example, is a spring located between body 34 and handle 42. In other embodiments, a round, leaf or other spring can be located between handle 42 and handle 44. In yet another embodiment, a piston can used to bias the pivot rod.

Insertion tool 32 can include features to increase ease of use such a ratchet 45 to prevent handles 42 and 44 from coming apart during surgery (e.g., to maintain an angle of rod retaining member 36 if the surgeon has to release handle 42). Additionally, insertion tool 32 can include guides 48 and 49 to guide a tool to rod retaining member 36 to release rod 30.

Rod insertion tool 32 may be made of materials including, but not limited to, titanium, titanium alloys, stainless steel, ceramics, and/or polymers. Rod insertion tool 32 can be autoclaved and/or chemically sterilized or be made of sterile materials.

Figure 2:
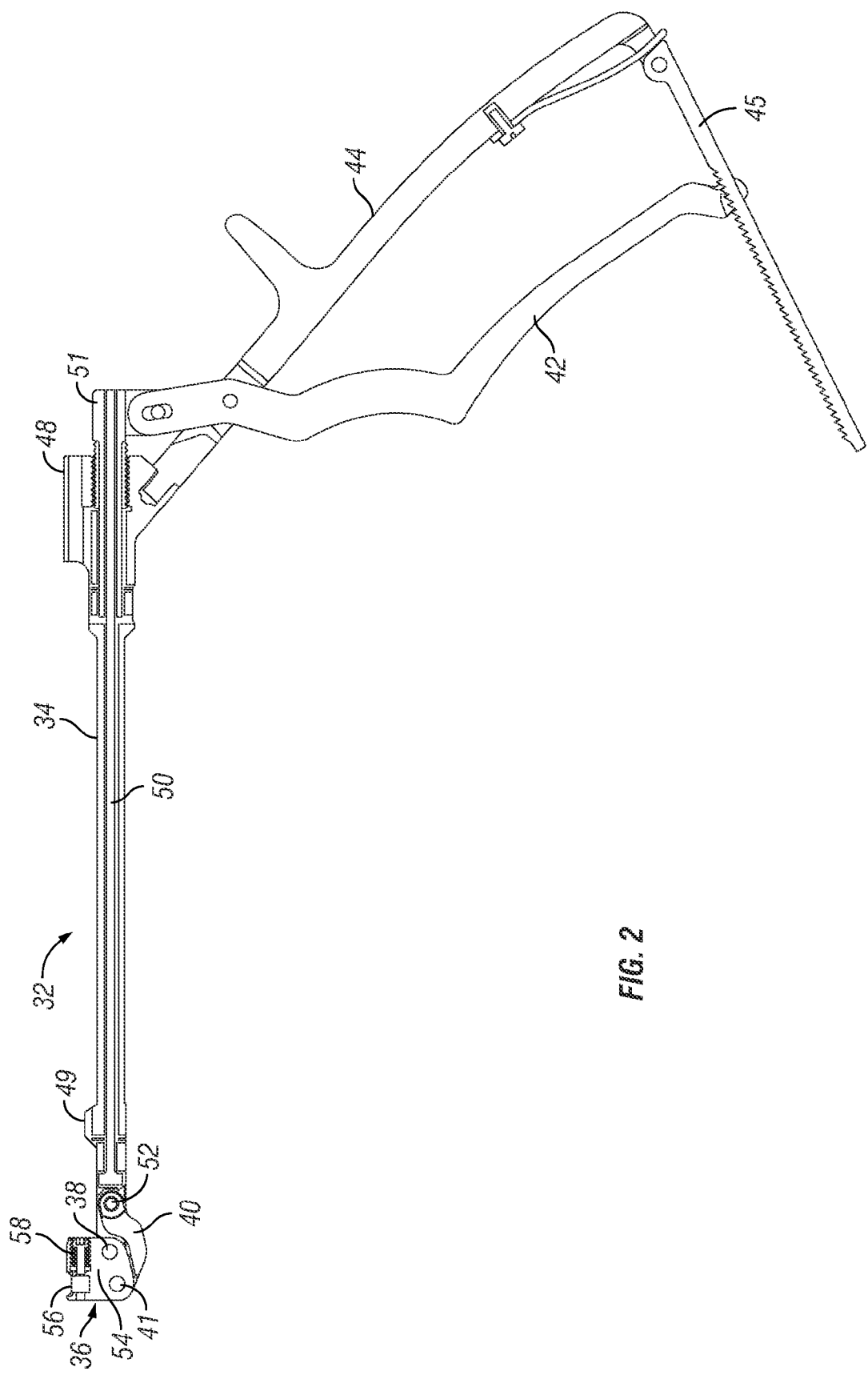
FIG. 2 is another diagrammatic representation of an embodiment of a rod inserter tool.

FIG. 2 is a cross sectional view of one embodiment of a insertion tool 32 illustrating body 34, rod retaining member 36, rotatable coupling 38, linkage 40, handle 42, handle 44, ratchet 45 and biasing member 46. In addition, FIG. 2 illustrates an embodiment of pivot rod 50 and an intermediate body 51. In this embodiment, pivot rod 50 is coupled to linkage 40 through a rotatable coupling 52, such as a pin, rivet, screw or other coupling that allows rotation between the components. At the other end, intermediate body 51 couples handle 42 to pivot rod 50 and provides a surface against which biasing member 46 can press. In other embodiments, handle 42 can be directly coupled to pivot rod 50 without an intermediate body. Similarly biasing member 46 can contact pivot rod 50 directly. Other suitable arrangements for placing pivot rod 50 in operational relationship with handle 42 or biasing member 46 can be employed.

Rod retaining member 36 can include a housing 54 defining cavity 56 sized and shaped to receive an end portion of a rod. According to one embodiment, the cavity and end portion of the rod can have a shape that prevents the rod from rotating about its length during insertion. For example, cavity 56 can have a square, rectangular, elliptical, or other noncircular cross section. However, in other embodiments, cavity 56 can be circular. In one embodiment, rod insertion tool 30 only engages the spinal stabilization rod at the end portion of the spinal stabilization rod inserted in cavity 56.

Rod retaining member 36 can also include a rod securing mechanism that holds rod 30 in place in rod retaining member 36. Examples of securing mechanisms include, but are not limited to, spring biased pins or balls that fit in indentions in the end portion of the rod, detents or indents the inhibit movement of the rod, a set screw or other mechanism. In the embodiment shown, housing 54 can include a threaded hole 58 into which a pin or set screw threads. In one embodiment, a set screw can translate in hole 58 until it contacts the rod or, alternatively, push a pin, ball or other member that contacts the rod. In another embodiment, a threaded pin can translate in hole 58 until the pin engages a portion the rod being secured.

In the configuration shown in FIG. 2, handles 42 and 44 are squeezed together resulting in rod retaining member being in a different position than in FIG. 1. If the handles are released, biasing member 46 can cause the handles to separate. Handle 42 will pull pivot rod 50 and linkage 40 to the right causing rod retaining member 36 to rotate counterclockwise unless ratchet 45 is engaged.

Figure 3:
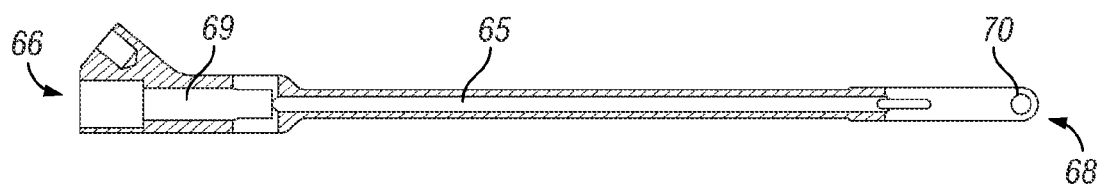
FIGS. 3 and 4 are diagrammatic representations of an embodiment of an outer body of a rod inserter tool.
Figure 4:
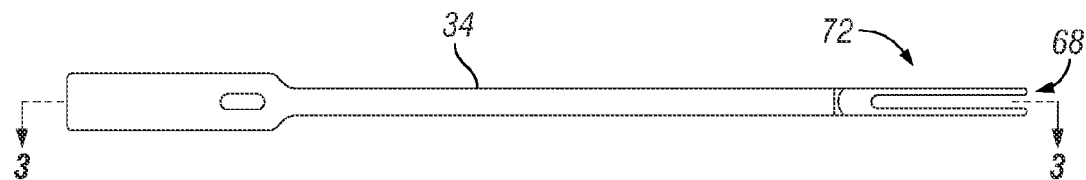

FIGS. 3 and 4 are diagrammatic representation of a first view of an embodiment of an outer body 34. Outer body 34 can include a passage 65 running from proximal end 66 and a distal end 68. Additionally, body 34 can include an area 69 into which intermediate body 51 can fit. In the embodiment of FIG. 3, a hole 70 near distal end 68 can be used to insert a pin or other member to couple rod retaining member 36 to body 34. FIG. 4 is a diagrammatic representation of another view of an embodiment of outer body 34 showing that, according to one embodiment, distal end 68 can include a forked section 72. Forked section 72 can be shaped to allow linkage 40 to move and provide a space for rod retaining member 36 to rotate. It should be noted, however, that other end configurations that allow rod retaining member 36 to rotate can be used.

Figure 5:
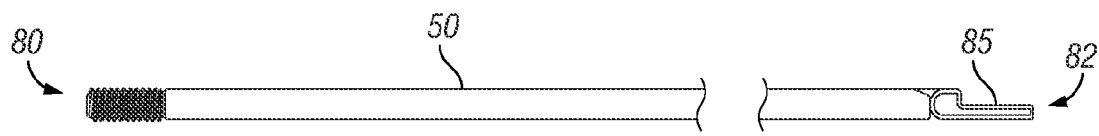
FIG. 5 is a diagrammatic representation of an embodiment of a pivot rod.

FIG. 5 is a diagrammatic representation of one embodiment of pivot rod 50 including proximal end 80 and distal end 82. Proximal end 80 can include a threaded section that allows pivot rod 50 to be threaded into intermediate body 51. Distal end 82 can include a coupling portion 85. In the embodiment of FIG. 5, the end portion of pivot rod 50 forms a coupling portion 85 having an "L" shaped flat section with a hole through which a pin, screw, rivet or other component can fit to form a rotatable coupling with linkage 40. In other embodiments, the end portion of pivot rod 50 can have any suitable shape for coupling to linkage 50.

Figure 6A:
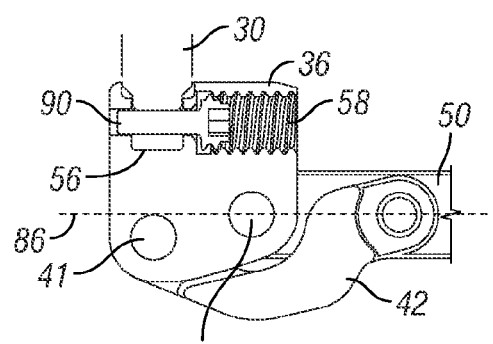
FIGS. 6A and 6B are diagrammatic representations of embodiments of rod retaining members.
Figure 6B:
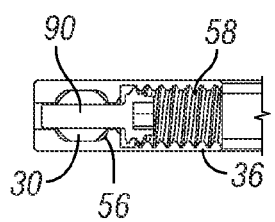

FIGS. 6A and 6B are cross sectional views of one embodiment of a rod 30, pivot rod 50, rod retaining member 36 and linkage 40. In this embodiment, linkage 40 has a curved or hook shape that connects to rod retaining member at position 41 that is offset a distance from the long axis 86 of pivot rod 50. This creates a moment arm about the axis formed by coupling 38 even if the rod 50 is in line with this axis of rotation for rod retaining member 36 relative to the outer body.

In the embodiment of FIG. 6A, rod retaining member 36 includes a pin 90 with a threaded section that screws in threaded hole 58. Pin 90 can pass all the way or partially through a portion of rod 30 to retain rod 30 in cavity 56. The square shape of cavity 56 and the end section of rod 30 prevent rod 30 from rotating in cavity 56 prior to rod 30 being secured with pin 90. Threaded hole 58 can be oriented so that the end of threaded hole 58 faces the user when the rod is in a final position. This can allow the user to unscrew pin 90 using a tool or otherwise disengage the rod securing mechanism.

Figure 7:
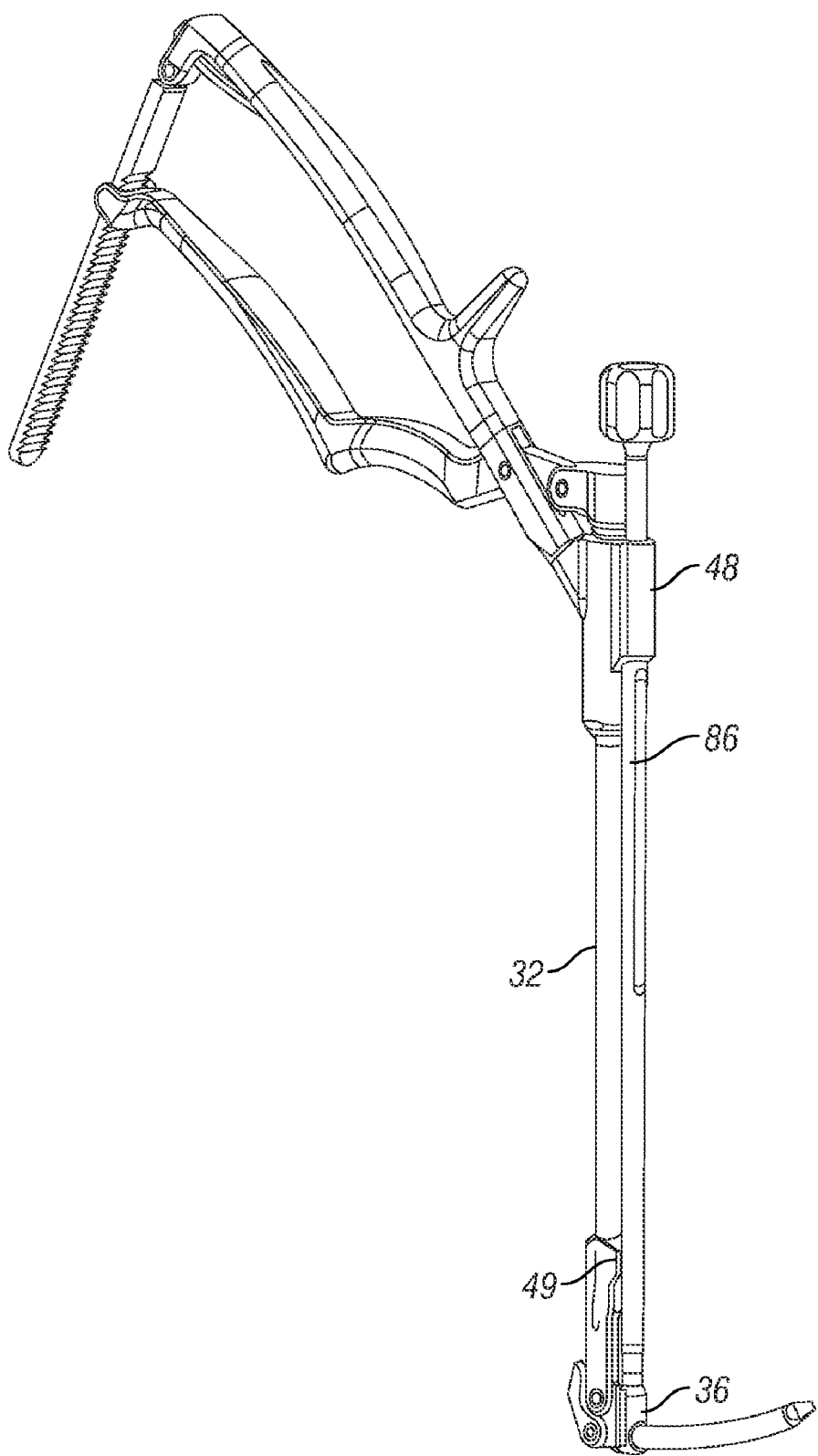
FIG. 7 is a diagrammatic representation of an embodiment of a rod insertion tool and an embodiment of a release tool.

FIG. 7 is a diagrammatic representation of one embodiment of rod insertion tool 32 having a release tool 86 guided to threaded hole 58 using guides 48 and 49. In the example of FIG. 7, release tool 86 can be screwdriver having a head that matches a corresponding slot or hole in pin 90. By way of example, but not limitation, tool 86 can be a Philips, flathead, star head, hex head or other shaped screwdriver. In other embodiments, the tool may simply be a pointed shaft or other shaped shaft that can allow release of the rod securing mechanism.

Figure 8A:
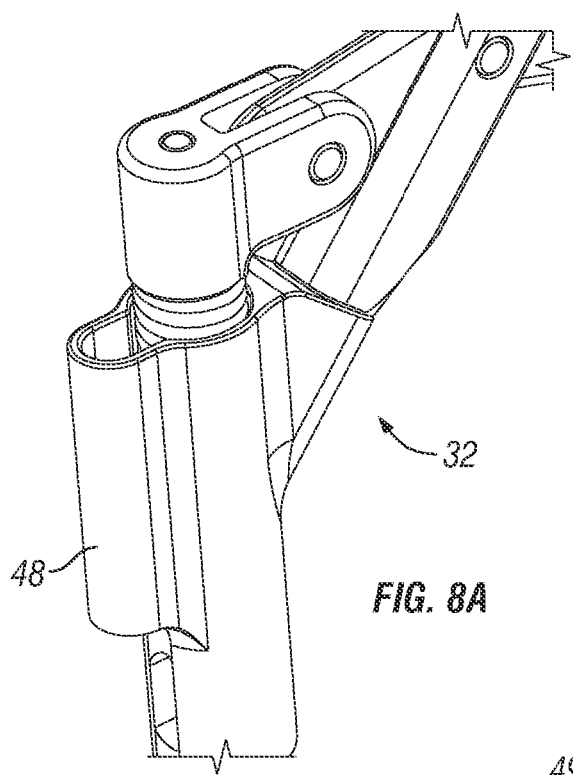
FIGS. 8A and 8B are diagrammatic representations of portions of an embodiment of a rod insertion tool.
Figure 8B:
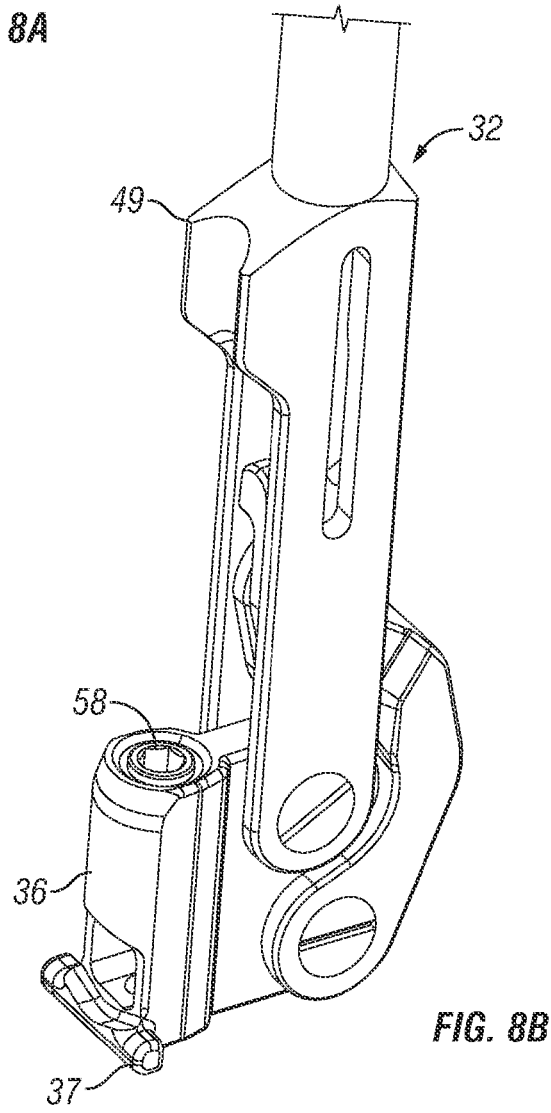

FIGS. 8A and 8B are diagrammatic representations of guides 48 and 49 at the proximal and distal portions of insertion tool 32. The guides 48 and 49 can be passages or channels or other features that aid in alignment of tool 86 with rod retaining member 36, and more particularly with the rod securing mechanism (in this example threaded pin 90). In other embodiments, guides 48 and 49 may include features such as slots or protrusions that match with complementary features on tool 86 to guide tool 86. Additionally, FIG. 8B illustrates a stopping feature 37 beneath cavity 56. The stopping feature 37 can be sized to be wider than a channel of a sleeve into which rod retaining member 36 fits. In one embodiment, consequently, rod retaining member 36 can fit partially into the channel in one orientation, while stopping feature 37 can prevent rod retaining member 36 from fitting into the channel in another orientation. This can help ensure, for example, that rod retaining member is offset from the head of a bone fastener when the stabilization rod is seated in the bone fastener so that a portion of the stabilization rod extends past the head of the bone fastener. The stopping feature can be an extension, ridge or other feature sized and positioned to allow rod retaining member 36 to fit in the channel of a sleeve in one orientation but prevent rod retaining member 36 from fitting in the channel in another orientation.

In operation, rod insertion tool 32 allows a rod to be inserted in an orientation with a reduced profile relative to the patient The rod insertion tool can guide the rod to a desired location and rotate the rod to span a set of bone fasteners. Because the rod can rotate after being inserted in the body, the rod can be guided under soft tissue above the portion of the spine being stabilized. This means that a large portion of the tissue above and between the vertebrae being stabilized does have to be opened to place the rod.

Figure 9:
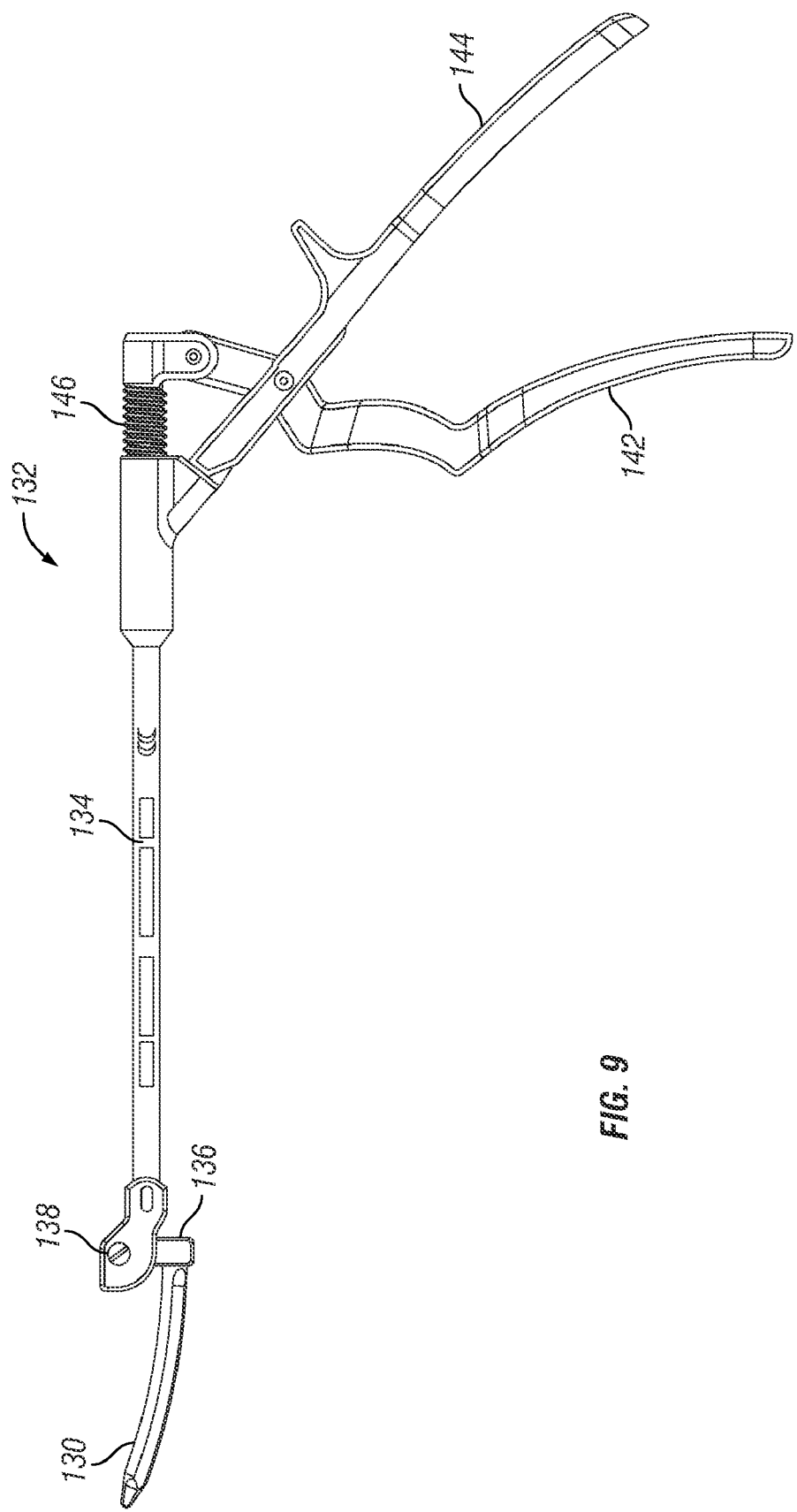
FIG. 9 is a diagrammatic representation of another embodiment of a rod insertion tool.

FIG. 9 is a diagrammatic representation of another rod 130 and insertion tool 132. Insertion tool 132 can include an outer body 134 that defines a passage for a pivot rod. A rod retaining member 136 is coupled to outer body 134 in a manner that allows rod retaining member 136 to rotate relative to outer body 134. As an example, a pin 138 can run through outer body 134 and rod retaining member 136 to create an axis of rotation for rod retaining member 136. The pivot rod can couple to rod retaining member 136 in a manner such that movement of the pivot rod 150 (shown in FIG. 10) in body 134 causes rod retaining member 136 to rotate from a first position to a second position through a range of angles. While insertion tool 132 can be configured for any range of angles, in a particular embodiment, the range of angles is from 0 degrees to 90 degrees from the axis of body 134. A linkage 140 (shown in FIG. 10) can connect to rod retaining member 136 at a rotatable coupling. Linkage 140 can also couple to the pivot rod 150.

A handle 142 can connect to the pivot rod such that movement of the handle causes the pivot rod to move. In the example of FIG. 9, handle 142 and handle 144 are in a Kerrison style arrangement such that squeezing handle 142 relative to handle 144 will cause the pivot rod to move forward. A biasing member 146 can be used to maintain the pivot rod in a particular position when a user does not squeeze handle 142. The biasing member, in this example, is a spring located between body 134 and handle 142. In other embodiments, a round, leaf or other spring can be located between handle 142 and handle 144. In yet another embodiment, a piston can used to bias the pivot rod.

FIG. 10 is a diagrammatic representation of one embodiment of a pivot rod 150 coupled to rod retaining member 136 by linkage 140. Pivot rod 150 can include a coupling portion at which pivot rod 150 can rotatably couple to linkage 140. In turn, linkage 140 can couple to rod retaining member 136 at a rotatable coupling. When pivot rod 150 moves in body 134, the force of pivot rod 150 is transferred to rod retaining portion 136 to cause rod retaining portion 134 to rotate relative to body 134.

FIG. 11 is a cross sectional view of another embodiment of rod retaining member 136. Rod retaining member 136 can include a cavity 152 that is shaped to receive the end portion of a rod 130. Additionally, rod retaining member 136 can include a rod securing mechanism to hold rod 130 in place in cavity 152. In this example, rod retaining member 136 can include a threaded hole 158 into which a threaded set screw or pin can fit. The threaded set screw or pin can contact or pass partially or all the way through the rod to hold rod 130 in place. Cavity 152 can be shaped to minimize rotation of rod 130 when inserted in cavity 152.

Figure 12:
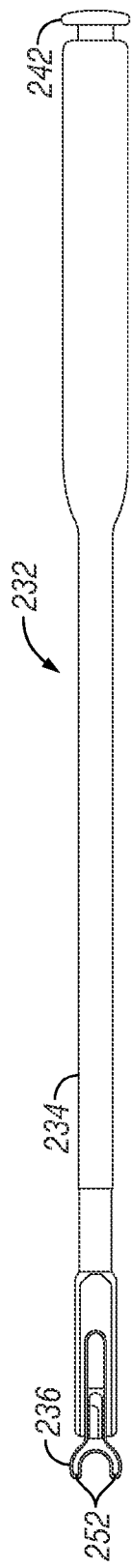
FIG. 12 is a diagrammatic representation of another embodiment of a rod insertion tool.
Figure 13A:
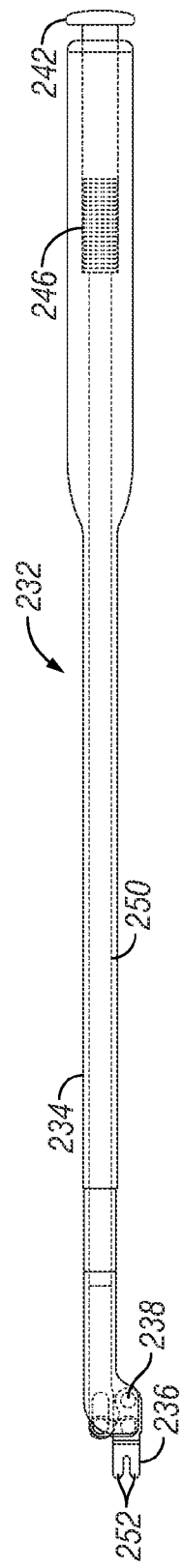
FIGS. 13A and 13B are views of the rod insertion tool of FIG. 12 in various orientations.
Figure 13B:
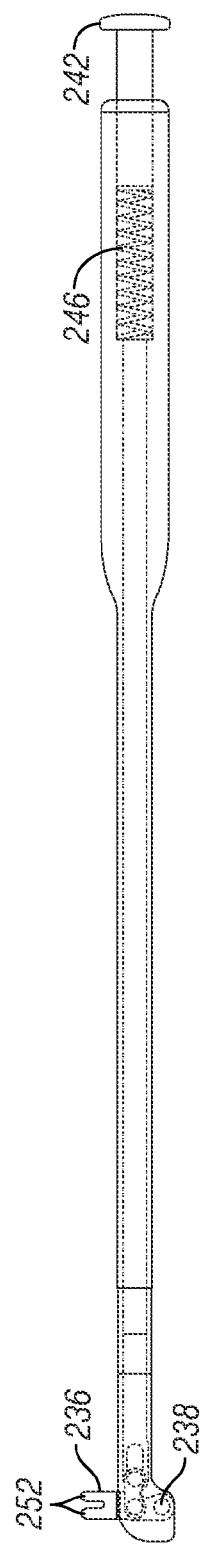

FIGS. 12-14 illustrate another embodiment of a rod insertion tool 232. In the embodiment of FIGS. 12, 13A and 13B, rod insertion tool 232 can include a body 234, rod retaining member 236, a pull handle 242, a biasing member 246 and a pivot rod 250. Rod retaining member 236 can couple to body 234 with a rotatable coupling 238. Movement of handle 242 can cause rod retaining member 236 to rotate relative to body 234. FIGS. 13A and 13B illustrate rod retaining member 236 in two positions corresponding to the positions of handle 242. A linkage 240 can also be coupled to both rod retaining member 236 and pivot rod 250 with rotatable couplings, as shown, for example, in FIG. 14.

In the embodiment of FIGS. 12-14, rod retaining member 236 can include two or more fingers 252 sized and shaped to fit around a rod. The fingers can be made of a material and shaped to act as springs so that the fingers open when pulled against the rod with sufficient force but otherwise grasp the rod.

FIGS. 15-16 are diagrammatic representations of another embodiment of a rod insertion tool 332 having a body 334, a rod retaining member 336, a handle 342, a pivot rod 350 and a linkage 340 between the pivot rod 350 and the rod retaining member 336. Rod retaining member 336 can be coupled to housing 334 with a rotatable coupling and link 340 can be coupled to pivot rod 350 and rod retaining member 336 with rotatable couplings. Linkage 340 is coupled to rod retaining member 336 at a position that allows rotation of rod retaining member as pivot rod 350 moves back and forth. Again, in this example, rod retaining member 336 can have fingers 353 that grasp the rod but can be pulled off the rod with sufficient force.

FIGS. 17-18 are diagrammatic representations of another embodiment of a rod insertion tool 432 having a body 434, a rod retaining member 436, a handle 442, a pivot rod 450 and a linkage 440 between the pivot rod 450 and the rod retaining member 436. Rod retaining member 436 can be coupled to housing 434 with a rotatable coupling and link 440 can be coupled to pivot rod 450 and rod retaining member 436 with rotatable couplings. Linkage 440 is coupled to rod retaining member 436 at a position that allows rotation of rod retaining member 436 as pivot rod 450 moves back and forth. In this example, a sliding pin can fit in slot 455 and couple to rod retaining member 436. Slot 455 and the sliding pin can aid in guiding the rotation of rod retaining member 436.

Rod retaining member 436 can have fingers 457 that are secured to a frame 459 using pins or screws 461. A spring internal to frame 459 can push ends of fingers 457 such that fingers 457 can release a rod when rod insertion tool is pulled perpendicular to the rod with sufficient force.

Figure 19:
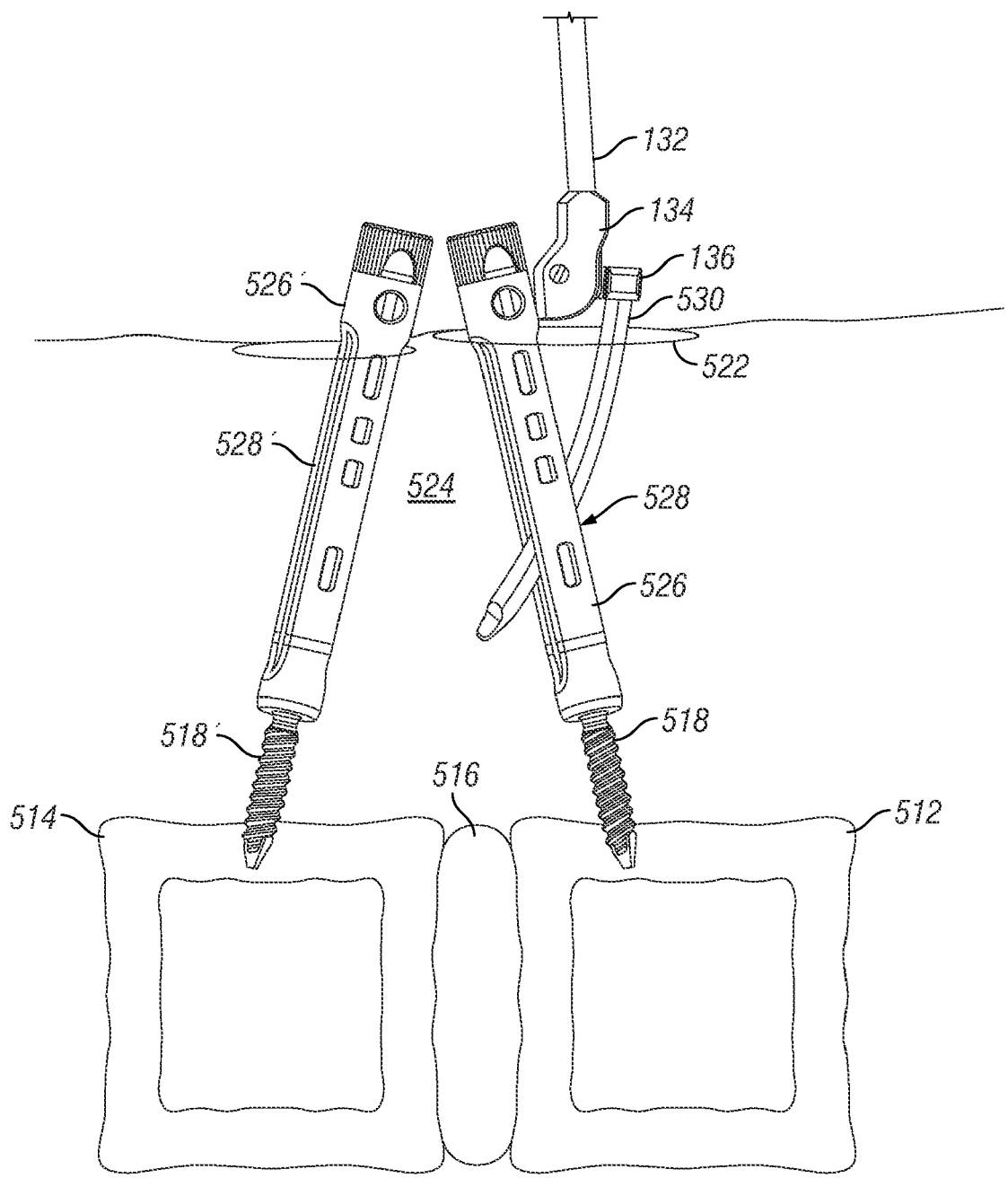
FIG. 19 is a diagrammatic representation of inserting a rod.
Figure 21C:
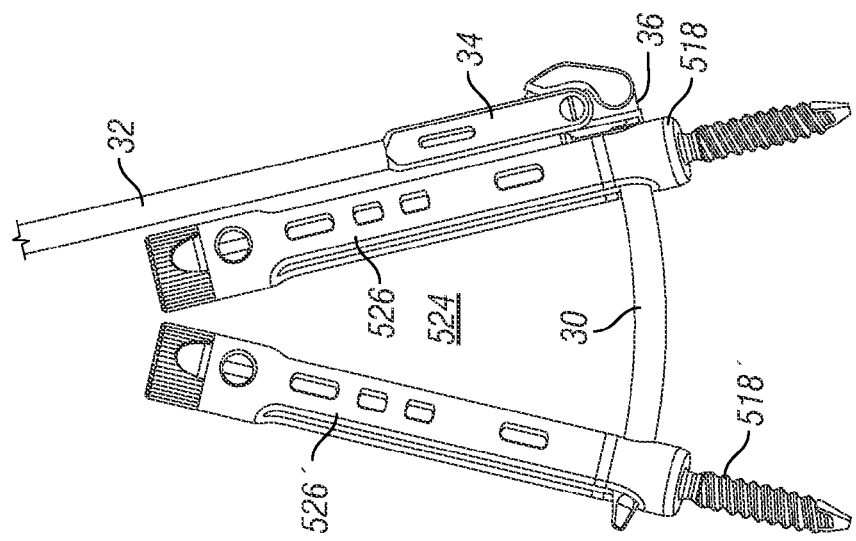
FIGS. 21A-21F are diagrammatic representations of inserting a rod and removing a rod insertion tool.
Figure 21B:
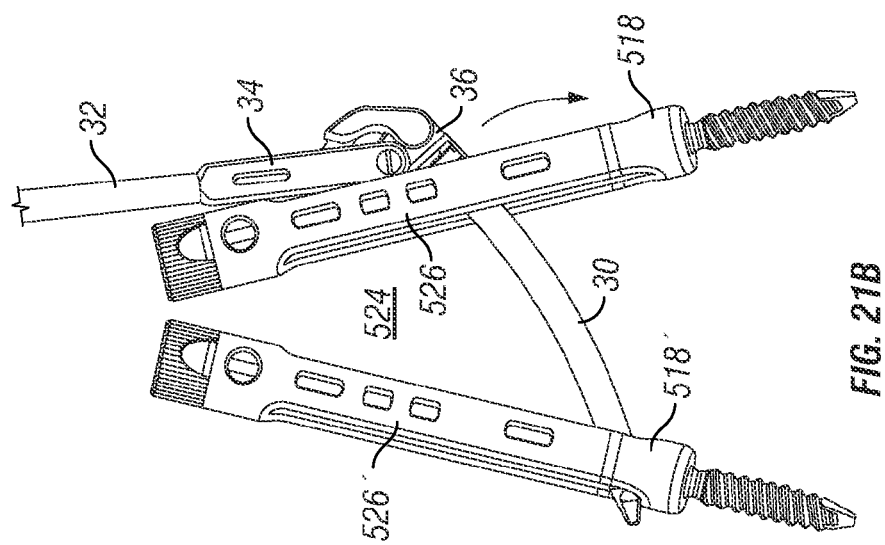
Figure 21A:
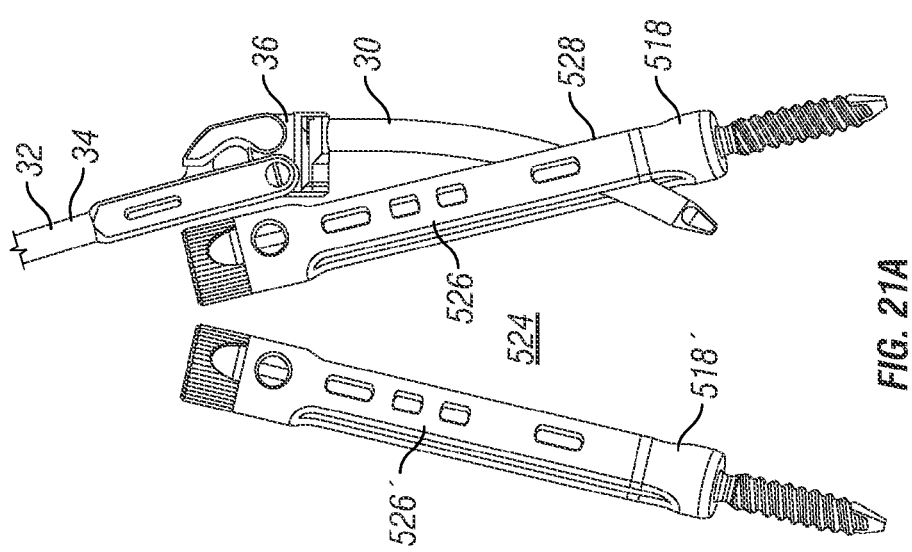
Figure 21D:
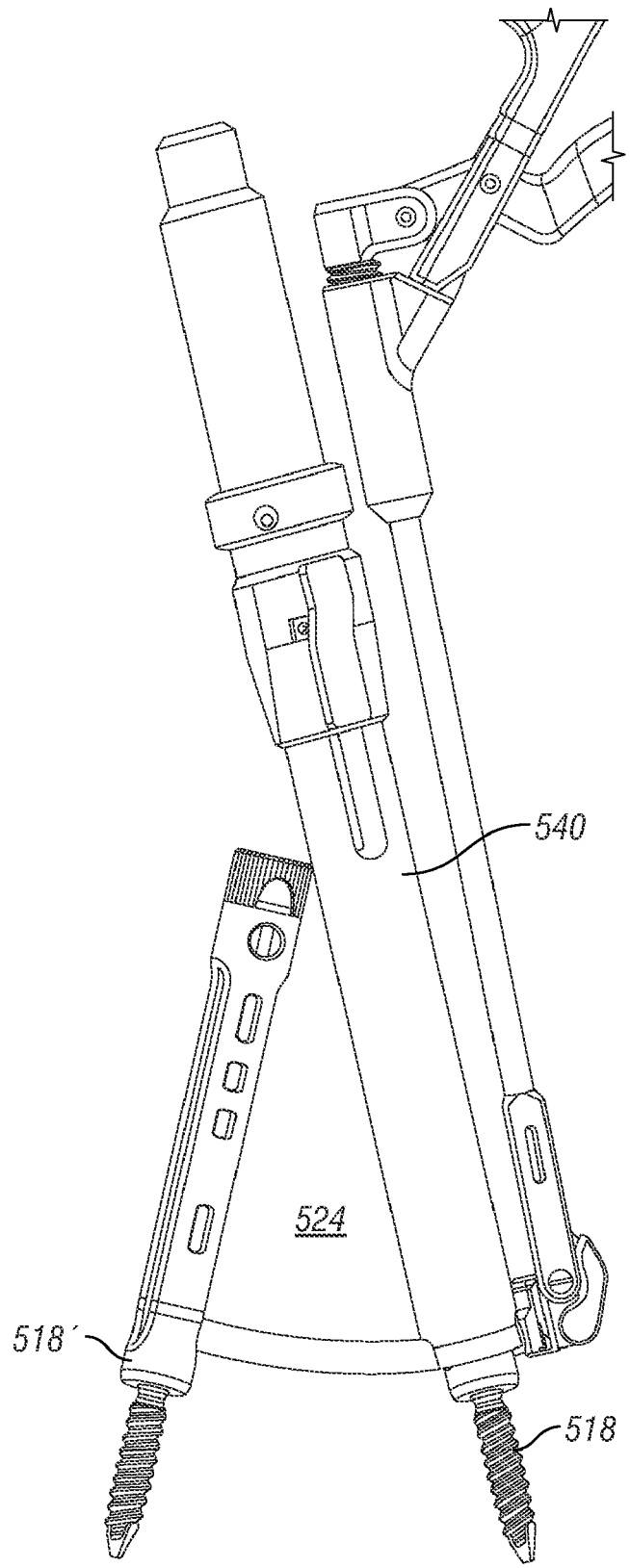
Figure 21F:
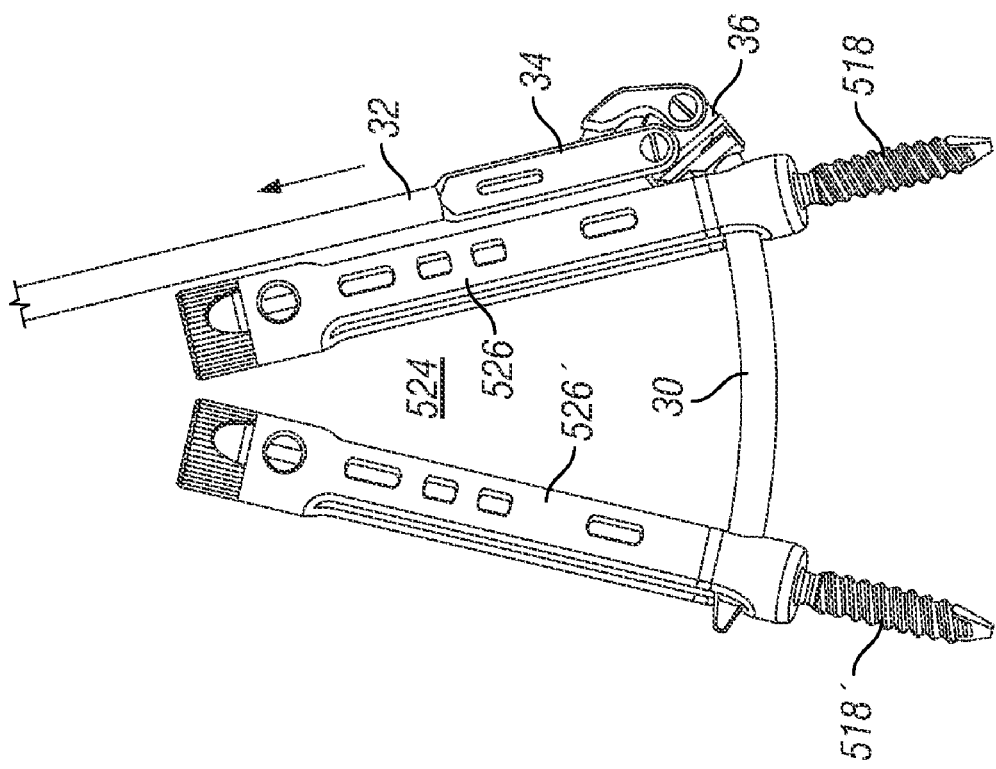
Figure 21E:
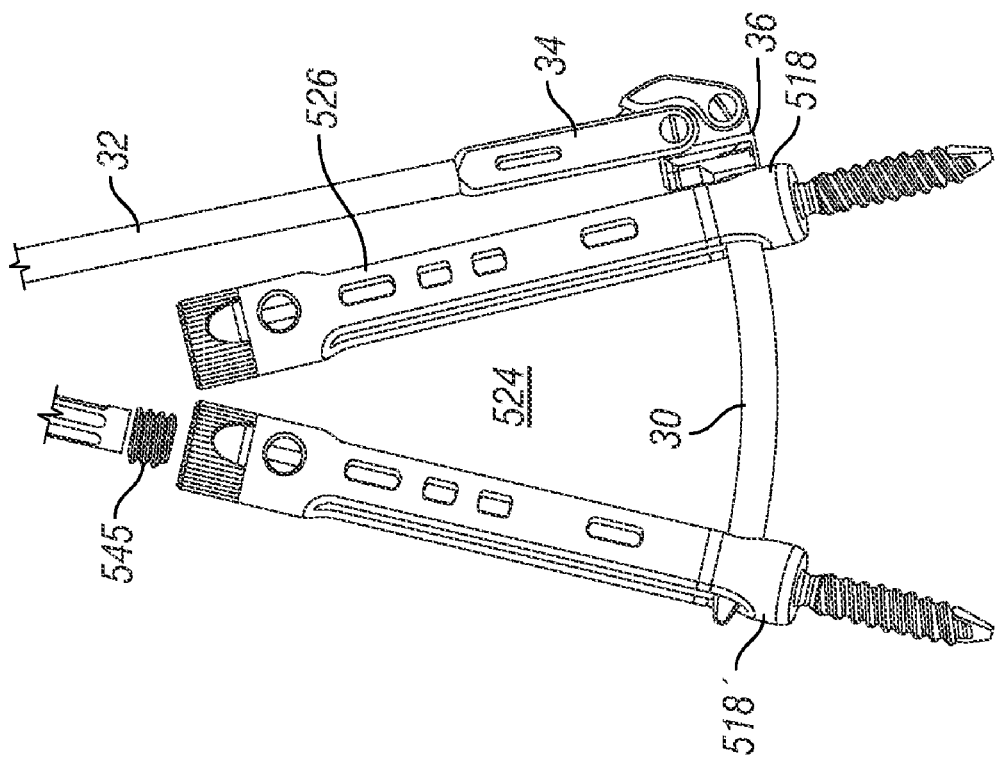

Rod insertion tools can be used to insert spinal stabilization rods to stabilize portions of the human spine. FIG. 19 is a diagrammatic representation of one embodiment of a human spine 500 having vertebra 512 and vertebra 514 separated by disc 516. FIG. 19 also depicts portions of a spinal stabilization system. As shown in this embodiment, fasteners 518 and 518' can be attached to vertebra 512 and vertebra 514. Fasteners 518 and 518' can include monoaxial screws, polyaxial screws, ring shank fasteners, barbs, nails, brads, trocars or other attachment devices. In other embodiments, fasteners 518 can be other types of fasteners that can secure a spinal stabilization rod.

Fasteners 518 and 518' can be inserted into the body through incision 522 using minimally invasive or other techniques. Soft tissue 524 may or may not be distracted to provide access to the surgical site. Sleeves 526 and 526' can provide working passages to fasteners 518 and 518' to provide access for various tool and allow a closure members to be guided to the fasteners. Example embodiments of sleeves include, but are not limited to, sleeves described in U.S. patent application Ser. No. 11/779,406 entitled "Spinal Stabilization Systems with Quick-Connect Sleeve Assemblies For Use In Surgical Procedures" by Landry et al., which is hereby fully incorporated by reference herein.

Sleeves 526 and 526' can further include side channels 528 and 528'. When sleeve 526 is coupled to fastener 518, channels 528 and 528' can align with a corresponding slot on fasteners 518 and 518'. Channel 528 can run from the distal end of sleeve 526 a selected distance. According to one embodiment, channel 528 can be long enough so that a portion of channel 528 extends outside of the patient's body during surgery. Each sleeve can include similar channels on one side or both sides. If sleeve 526 has channels on both sides, the channels can be the same or different lengths.

Using minimally invasive procedures, a rod can be inserted into the body in manner that minimizes the size of incision 522, reduces damage to soft tissue 524 and does not require additional incisions some distance from incision 522. According to one embodiment, a trial rod 530 can be used to create a passage through tissue 524 for the spinal stabilization rod prior to implantation of the spinal stabilization rod. The trial rod can have a tapered end, dilated inferior surface or other features to more easily displace tissue. Trial rod 530 can be inserted using a rod insertion tool such as rod insertion tool 32 or 132 or other embodiment of rod insertion tool. In the embodiment shown, rod insertion tool 132 is moved into the body with trial rod 530 in a first position that has a smaller profile entering the patient. A portion of body 134 and/or rod retaining member 136 can be inserted into a channel 528 (in this case on the outer side of the surgical site). Rod insertion tool 132 can be moved into the body until the trial rod is in a desired position and used to rotate trail rod 530 to a desired orientation.

FIGS. 20A-C illustrate one embodiment of placement of trial rod 530. When trial rod 530 has reached a desired position, rod retaining member 136 can be rotated so that trial rod 530 spans the distance to fastener 518'. Rod 530 can be guided with the aid of fluoroscopy or other imaging technique. According to one embodiment, insertion tool 132 can be moved downward to seat a portion of trial rod 530 in fastener 518. Housing 234 in this example is narrow enough to fit in the channel of the sleeve 526 thereby taking up less additional space as rod 530 is guided into the body. Consequently, damage to or displacement of tissue by insertion tool 132 can be minimized. For example, because trial rod 530 can be inserted from the outside of sleeve 526, soft tissue 524 undergoes minimal movement. Trial rod 530 can be removed from the body when an adequate passage for spinal stabilization rod 30 has been made.

FIGS. 21A-F illustrate one embodiment of placement of a spinal stabilization rod 30 using a rod insertion tool 32. Prior formation of a passage using a trial rod is optional. Percutaneous rod calipers or other measurement technique can be used to determine the desired length of rod 30 and whether a straight or bent rod should be used. A reshaped rod can be used or a rod bender can contour a straight rod as needed.

The selected rod 30 can be secured in rod retaining member 36 for insertion. In the embodiment shown, rod insertion tool 32 is moved into the body with rod 30 in a first position that reduces the profile of rod 30 entering the incision. A portion of rod retaining member 36 and/or body 34 can be inserted into a channel 528. Rod insertion tool can be moved into the body until rod 30 is in a desired position and rod 30 rotated into place so that rod 30 spans fasteners 518 and 518'. If needed, insertion tool 32 can be moved further downward during or after rotation of the rod so that rod 30 seats in the collar of fastener 518. Placement of rod 30 can be confirmed using fluoroscopy or other imaging technique.

In some cases, it may not be possible to fully seat rod 30 in fastener 518 or 518'. A reducer 540 (shown in FIG. 21D) can be used to persuade the rod into the head of fastener 518 or 518'. Any suitable reducer known or developed in the art can be used. The rod can also be moved to ensure correct lordotic orientation and desired extension beyond fasteners 518 and 518'. When rod 30 is in place, closure members, such as closure member 545 can be used to secure rod 30 in the fasteners 518 and 518' (illustrated in FIG. 21E). A release tool 86 can release rod 30 from insertion tool 32 so that insertion tool 32 can be removed. During removal a portion of rod retaining member 36 or body 34 can be moved along the channel in sleeve 526.

As can be seen in FIGS. 21A-21F, the rod can be inserted in a way that passes under a large amount of tissue 524. Consequently, tissue 524 does not have to be fully opened to place rod 30. While various steps for a method of inserting rod 30 percutaneously are shown the steps can be done in any order as needed or desired.

Figure 22B:
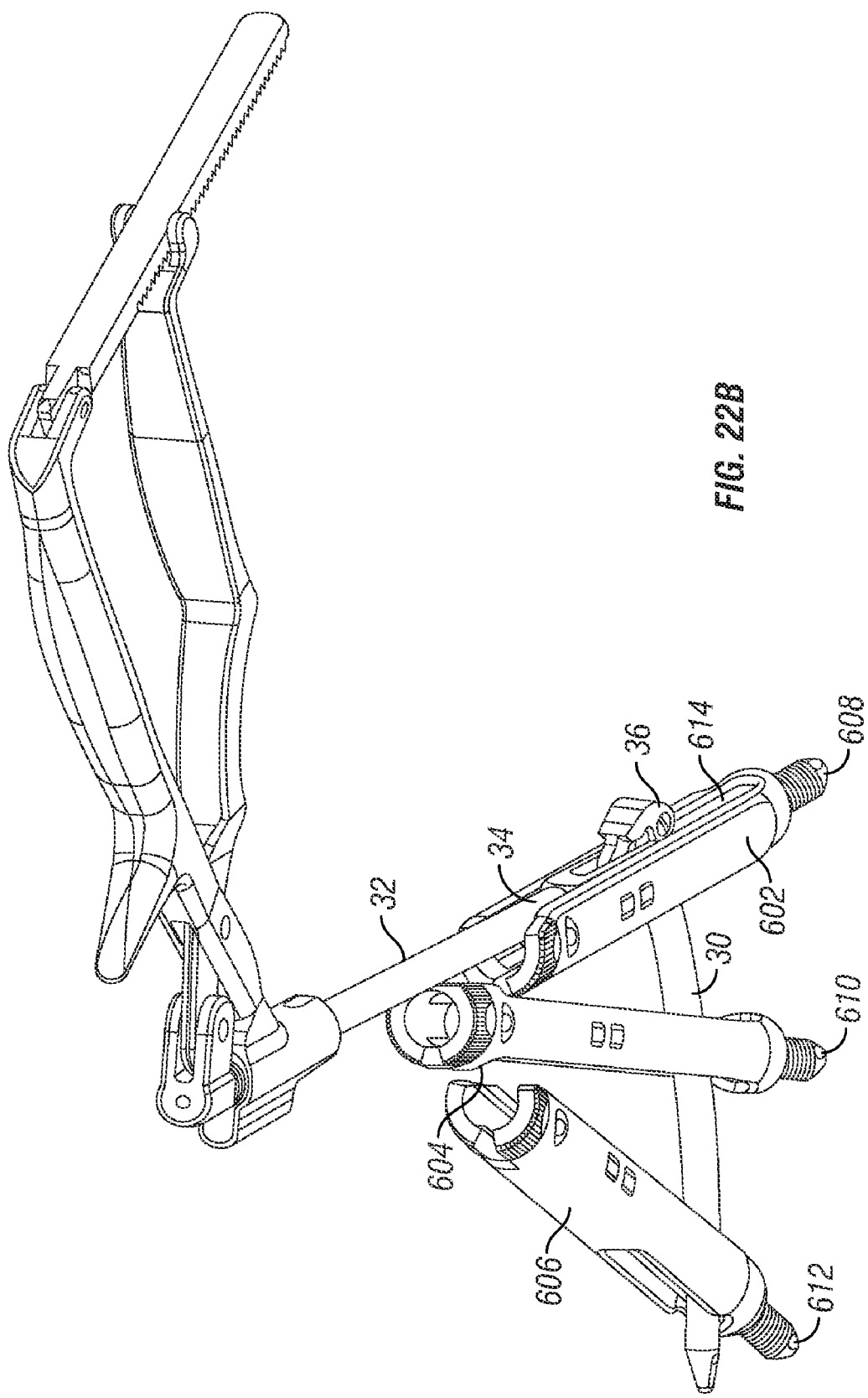
Figure 22C:
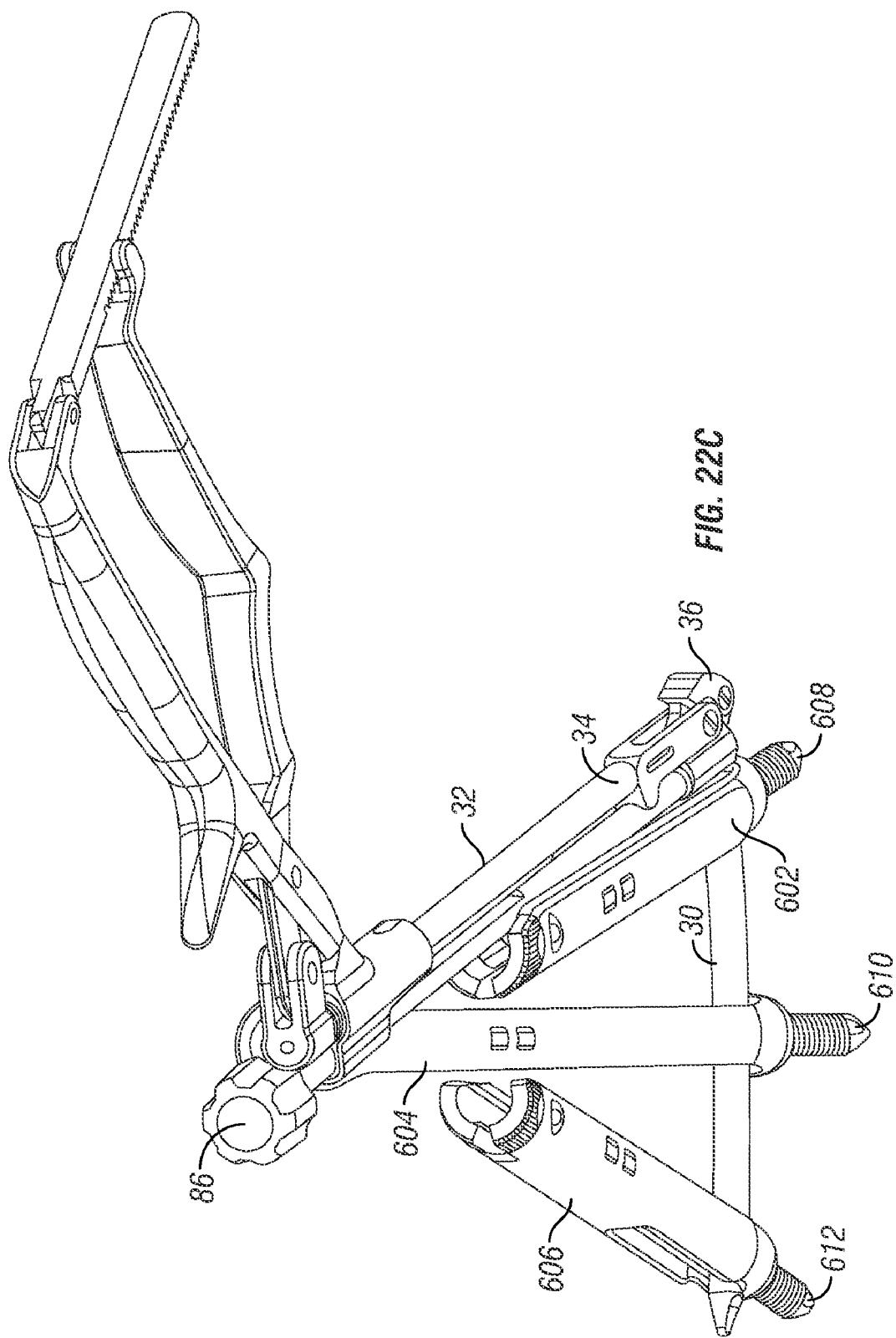
Figures 22D, 22E:
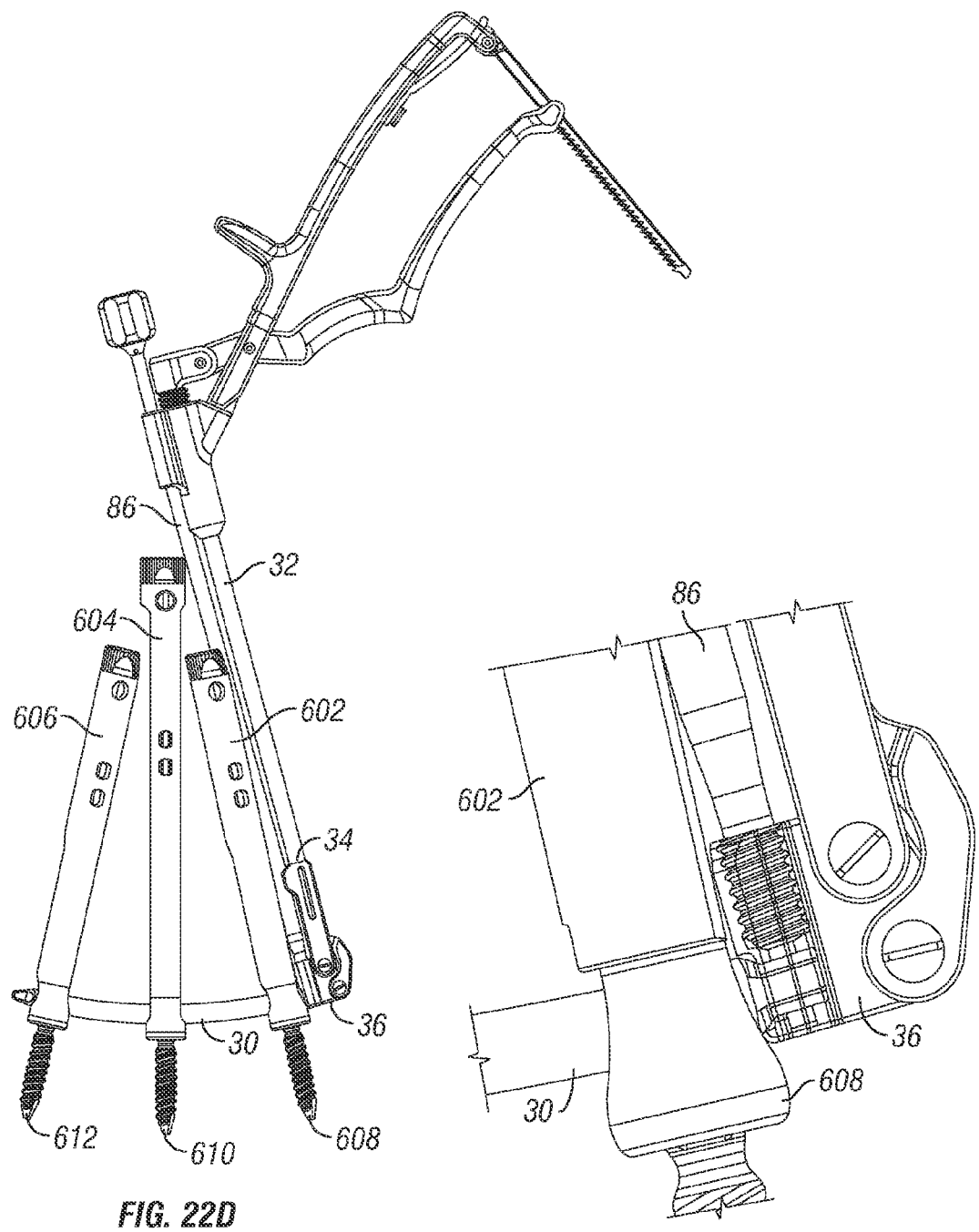
Figures 22F, 22G:
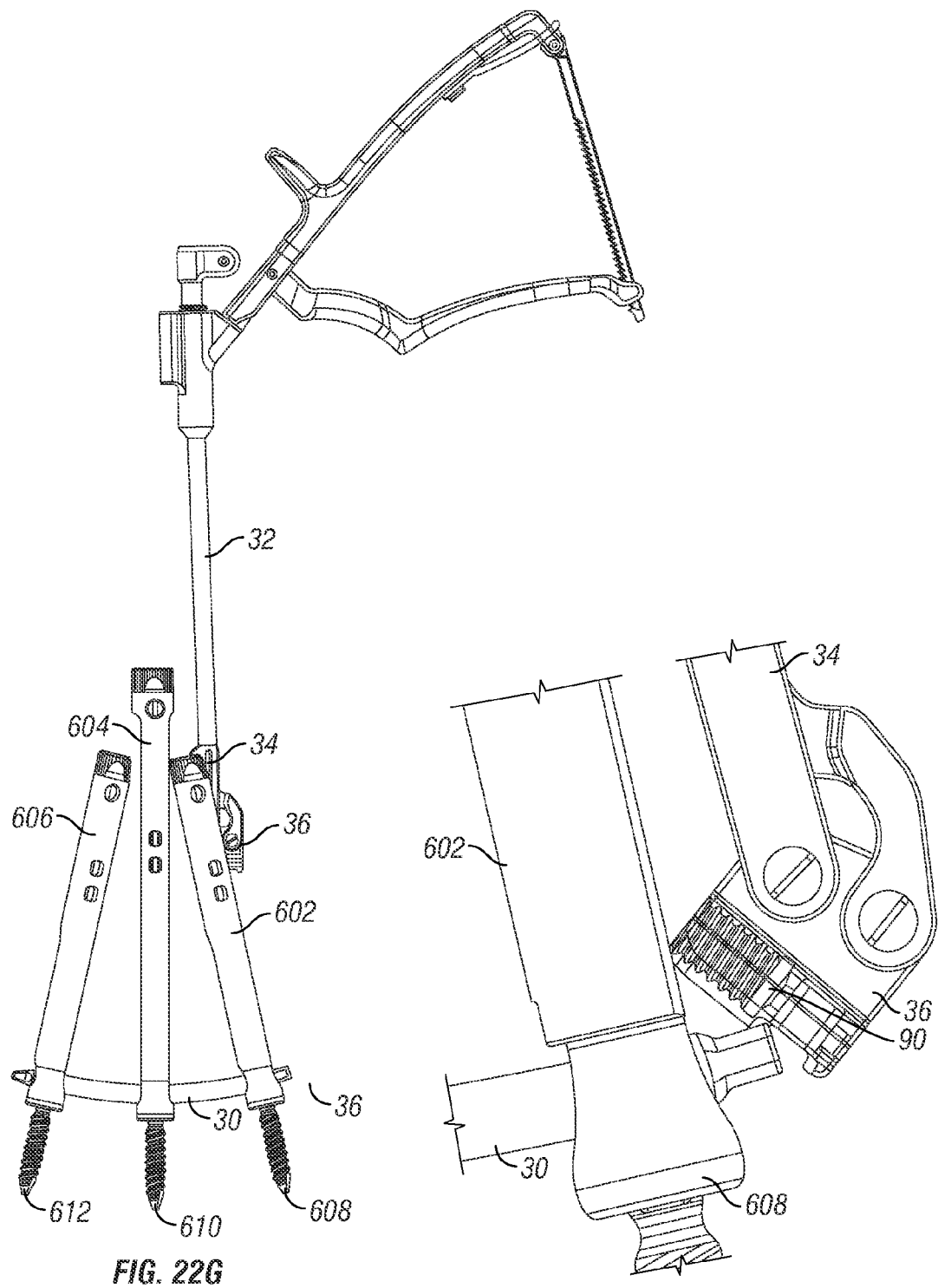

FIGS. 21A-21F illustrate insertion of rod 30 for a single level. Embodiments of rod insertion tools can insert rods in spinal stabilization systems for multilevel spinal stabilization systems. FIGS. 22A-G are a diagrammatic representation of a multilevel spinal stabilization procedure. In the example of FIGS. 22A-G, sleeves 602, 604 and 606 are attached to the heads of pedicle screws 608, 610 and 612 respectively. Rod 30 can be inserted into the patient with rod 30 in a first orientation that reduces the profile of rod 30 relative to the patient. During insertion, rod 30 can optionally pass partially or all the way through sleeve 602. When rod 30 is in a desired position, rod retaining member 36 can be rotated causing rod 30 to rotate. Rod retaining member 36 can also be moved downward toward fastener 608 during or after rotation of the rod to the second orientation. FIG. 22B illustrates moving rod 30 downward with body 34 and rod retaining member 36 passing through channel 614. When rod 30 is seated in at least fastener 608, as shown in FIGS. 22C-E, and a closure member secured, release tool 86 can be used to release rod 30 from rod retaining member 36. As shown in FIGS. 22F-G, when rod 30 has been released (e.g., by unscrewing pin 90), rod insertion tool 32 can be removed. As shown in FIG. 22G, a portion of insertion tool 32 can pass through channel 614 during removal.

While a user may guide the rod insertion tool by hand, the user can also stabilize the rod insertion tool using an adapter configured to detachably couple the rod insertion tool to the sleeve. FIGS. 23A and 23B illustrate one embodiment of using an adapter 700 to control the depth of rod insertion tool 232. Adapter 700 can include an insertion tool holding portion 702 and a sleeve mounting portion 704. According to one embodiment, sleeve mounting portion 704 can be sized to fit in a sleeve 706. Tool holding portion 702 can include a passage through which rod insertion tool 232 (or other rod insertion tool) fits and can include a mechanism for holding rod insertion tool 232 in place. Any suitable mechanism such as an interference fit, spring loaded contact member (for example actuated by a release button 708) or other mechanism can be used. According to an embodiment, rod insertion tool 232 can include depth markings so that the depth of rod insertion tool 232 is known relative to adapter 700. In one embodiment, adapter 700 can allow the rod insertion tool to be angled so that a portion of the rod insertion tool travels down a channel through a side of the corresponding sleeve.

Figure 24:
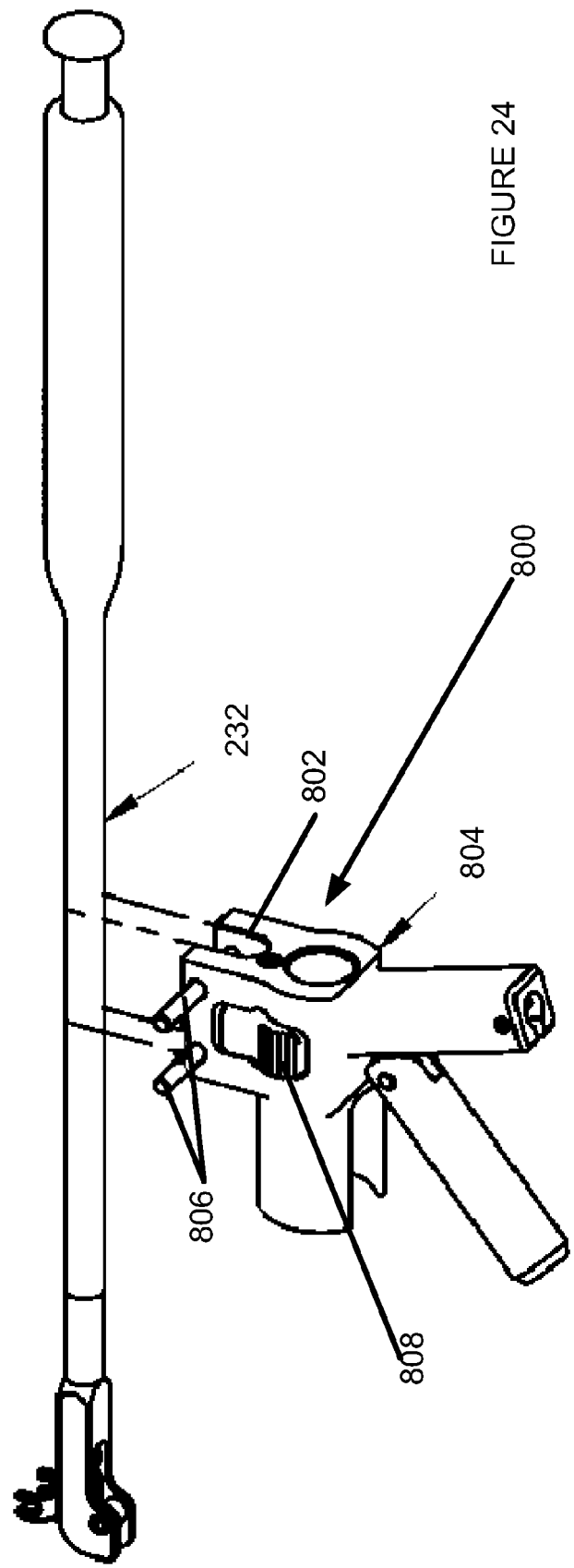
FIG. 24 is a diagrammatic representation of one embodiment of a rod insertion tool and an adapter.

FIG. 24 illustrates another embodiment of an adapter comprising an adapter body 800 having a portion 802 to removably couple to a rod insertion tool (e.g., rod insertion tool 232 or other insertion tool) and a mount 804 that fits in a sleeve to couple the rod insertion tool to the sleeve. A spring or otherwise biased member can push rod insertion tool 232 against pins 806 to hold the rod insertion tool in place. The member can be fully or partially disengaged by actuation of button 808 to allow rod insertion tool 232 to move up or down.

While embodiments previously described illustrate inserting a rod from the outer side of a sleeve, FIG. 25, on the other hand, illustrates an embodiment for inserting a rod from the inner side of sleeve 900. The rod can be brought down an inner channel of sleeve 900 until at a desired position and rotated to span the bone fasteners. While or post rotation, a portion of the rod can be seated in the head of one of the anchors and a closure member used to secure the rod. The rod also be seated in the other anchor and secured. Seating of the rod can include reduction. While the embodiment of FIG. 25 is shown with respect to rod insertion tool 232, other embodiment of rod insertion tools can be used to insert a rod from the inner side of sleeve 900.

FIG. 26 illustrates using a rod insertion tool in conjunction with other tools such as dilators. For example, a rod insertion tool (such as rod insertion tool 232 or other rod insertion tool) can be used in conjunction with a shaped dilator 950 to insert a rod. The dilator can be a dilator such as described in U.S. patent application Ser. No. 11/770,366, entitled "Stabilization System and Method" filed on Jun. 28, 2007, by Miller et al., which is hereby fully incorporated by reference herein.

Figure 27A:
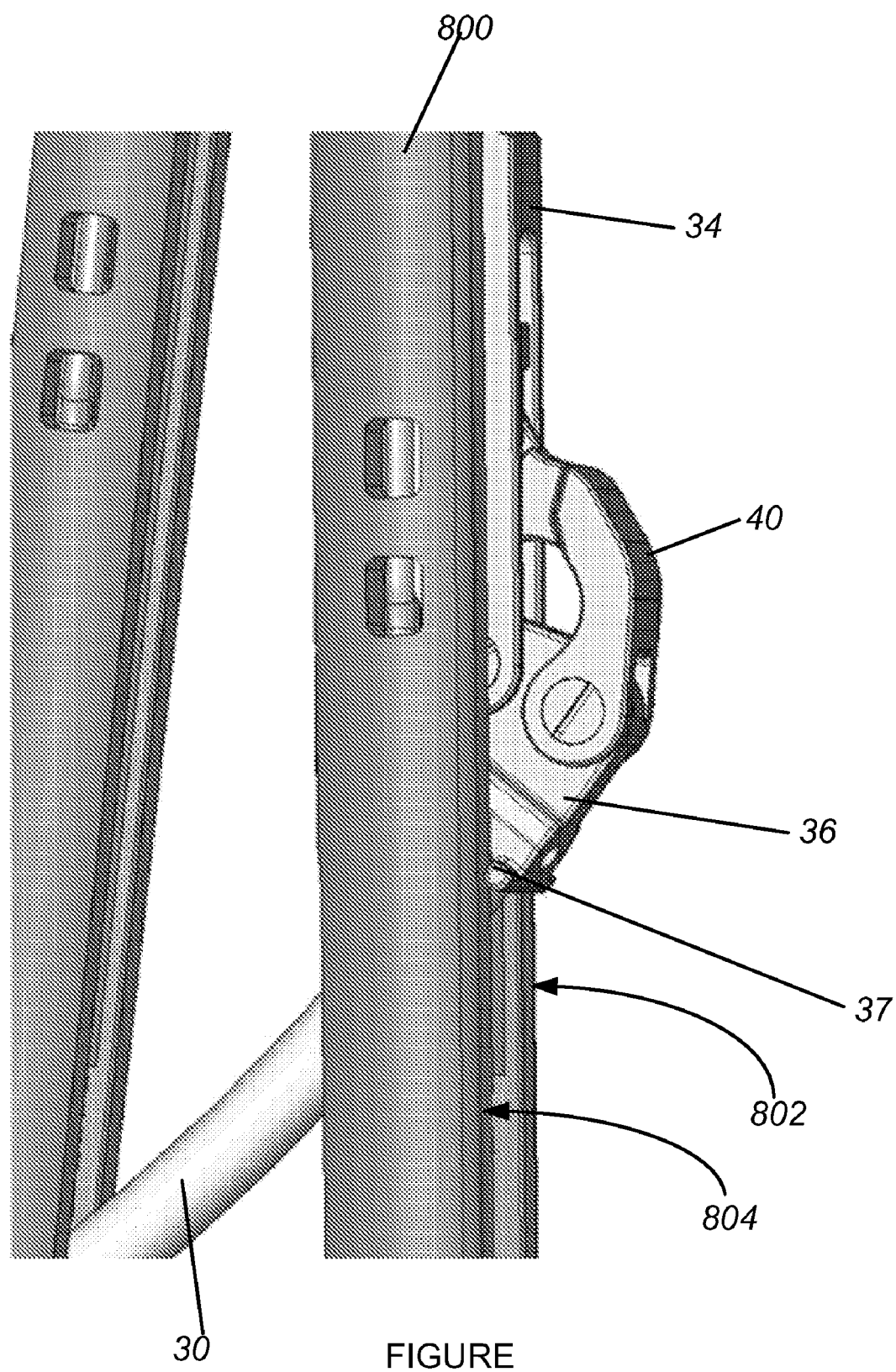
FIG. 27A-B are diagrammatic representation of inserting a rod with an embodiment of an insertion tool having a stopping feature.
Figure 27B:
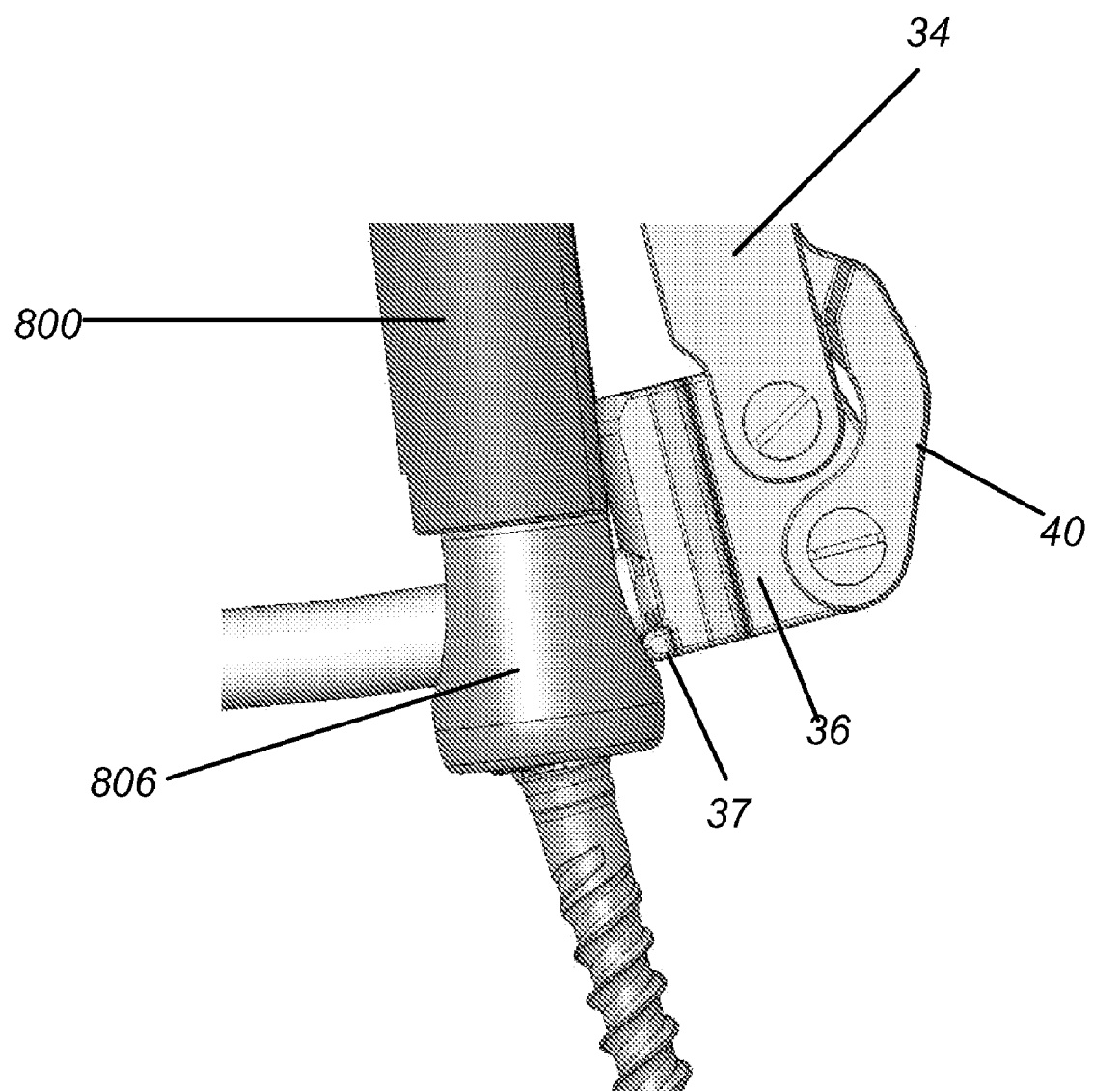

FIGS. 27A and 27B illustrate inserting a rod 30 using an insertion tool with a stopping feature 37. FIG. 27A illustrates a portion of tool body 34, rod retaining member 36, and a linkage 40. As shown in the embodiment of FIG. 27A, the insertion tool can be used to insert rod 30 from the outside of sleeve 800 relative to the surgical site. Stopping feature 37 is wider than the channel in the side of sleeve 800 (and corresponding slot of the bone fastener) so that stopping feature 37 contacts sleeve 800 at engaging surfaces 802 and 804. Stopping feature 37 can be positioned so that a portion of rod retaining member 36 can fit in the channel in the side of sleeve 800 when rod retaining member 36 is in particular orientations. In one example, stopping member 37 can be positioned so that rod retaining member 36 can partially fit in the channel when in an initial orientation in which the rod has a reduced profile when inserted.

FIG. 27B illustrates a portion of tool body 34, rod retaining member 36 and linkage 40. In the embodiment of FIG. 27B, rod retaining member 36 is in a second orientation in which rod 30 is seated in collar 806 to span the sleeves. Stopping feature 37 maintains the rod retaining member 36 in a position relative to collar 806 so that the end of rod 30 is outside of collar 806 when rod 30 is seated in collar 806. Use of stopping feature 37 allows proper rod placement and controls positioning of the rod insertion tool during surgery. This helps ensure that rod 30 extends through collar 806 when the closure member is secured.

In the foregoing specification, the disclosure has been described with reference to specific embodiments. However, as one skilled in the art can appreciate, embodiments of the insertion tools and methods disclosed herein can be modified or otherwise implemented in many ways without departing from the spirit and scope of the disclosure. Accordingly, this description is to be construed as illustrative only and is for the purpose of teaching those skilled in the art the manner of making and using embodiments of a dynamic stabilization rod. It is to be understood that the forms of the disclosure herein shown and described are to be taken as exemplary embodiments. Equivalent elements or materials may be substituted for those illustrated and described herein. Moreover, certain features of the disclosure may be utilized independently of the use of other features, all as would be apparent to one skilled in the art after having the benefit of this description of the disclosure.

What is claimed is:

1. A rod insertion system comprising:
   a bone anchor comprising a collar with a slot to receive a rod;
   a sleeve coupled to the collar having a channel in a side open to the slot, the sleeve comprising one or more engaging surfaces next to the channel;
   a spinal stabilization rod;
   a rod insertion tool comprising:
      an outer body defining a passage;
      a pivot rod translatable in the passage of the outer body;
      a rod retaining member sized to fit at least partially through the channel in the side of the sleeve and engaged to an end portion of the spinal stabilization rod, the rod retaining member coupled to the outer body and rotatable relative the outer body about an axis of rotation, the rod retaining member comprising:
         a stopping feature sized to contact the one or more engaging surfaces of the sleeve, the stopping feature including an extension that is wider than the channel and positioned to allow the rod retaining member to fit at least partially through the channel in the side of the sleeve when the rod retaining member is in a first orientation and maintain the rod retaining member in a position relative to the collar so that the end portion of the spinal stabilization rod passes outside of the collar when the rod retaining member is in a second orientation;
         a linkage coupled to the rod retaining member and an end portion of the pivot rod so that the rod retaining member rotates about the axis of rotation when the pivot rod translates relative to the outer body;
   wherein the rod insertion tool only engages the spinal stabilization rod at the end portion of the spinal stabilization rod.

2. The rod insertion system of claim 1, wherein the rod retaining member further comprises:
   a housing defining a cavity shaped to receive the end portion of the spinal stabilization rod, wherein the cavity is shaped to inhibit rotation of the spinal stabilization rod when the end portion of the spinal stabilization rod is in the cavity; and
   a rod securing mechanism adapted to prevent the end portion of the spinal stabilization rod from leaving the cavity.

3. The rod insertion system of claim 2, wherein the housing defines a threaded hole and the rod securing mechanism comprises a threaded pin.

4. The rod insertion system of claim 3, wherein the rod retaining member is rotatable relative to the outer body so that a head portion of the threaded pin faces a user when the rod retaining member is in a first position.

5. The rod insertion system of claim 1, wherein a portion of the outer body is sized to fit in the channel.

6. The rod insertion system of claim 1, wherein the linkage couples to the rod retaining member at a position offset from the axis of rotation.

7. The rod insertion system of claim 6, wherein the pivot rod is aligned with the axis of rotation and the linkage has a curved shape.

8. The rod insertion system of claim 1, further comprising a handle coupled to the pivot rod and adapted to assert a force on the pivot rod in a first direction.

9. The rod insertion system of claim 8, further comprising a biasing member adapted to assert a force on the pivot rod in a second direction opposite the first direction.

10. A method of inserting a spinal stabilization rod comprising:
   coupling an end portion of a spinal stabilization rod to a rod retaining member of a rod insertion tool external to a human body, wherein the rod insertion tool only engages the spinal stabilization rod at the end portion of the spinal stabilization rod;

providing a first sleeve coupled to a first bone fastener that is coupled to a first vertebrae of the human body and a second sleeve coupled to a second bone fastener that is coupled to a second vertebrae of the human body, wherein the first and second bone fasteners comprise collars to receive the spinal stabilization rod;

inserting the spinal stabilization rod into the human body through an incision using the rod insertion tool, wherein the rod retaining member is in a first orientation with the rod having a reduced profile when inserted;

contacting a stopping feature of the rod retaining member with one or more engaging surfaces on the first sleeve so that the rod retaining member at least partially fits in a channel in a side of the first sleeve, wherein the stopping feature includes an extension that is wider than the channel;

moving the spinal stabilization rod into the human body using the rod insertion tool with the rod retaining member partially in the channel;

moving a pivot rod internal to an outer body of the rod insertion tool to cause the rod retaining member to rotate about an axis of rotation formed by a rotatable coupling between the rod retaining member and the outer body of the rod insertion tool to position the rod retaining member in a second orientation with the spinal stabilization rod spanning the first and second bone fasteners, wherein when the rod retaining member is in the second orientation, the stopping feature maintains the rod retaining member in a position relative to the collar of the first bone fastener so that the end of the spinal stabilization rod extends past the collar; and releasing the spinal stabilization rod from the rod retaining member after the spinal stabilization rod is secured to at least one of the bone fasteners.

11. The method of claim 10, further comprising withdrawing the rod insertion tool from the human body, wherein at least a portion of the rod insertion tool travels up the channel in the side of the first sleeve during the withdrawal.

12. The method of claim 10, wherein the spinal stabilization rod is inserted percutaneously.

13. The method of claim 10, wherein the incision is the same incision through which the first sleeve passes.

14. The method of claim 13, wherein the second sleeve enters the human body through a separate incision.

15. The method of claim 13, wherein at least a portion of soft tissue between the first sleeve and second sleeve remains intact during insertion of the spinal stabilization rod.

16. The method of claim 10, further comprising using an adapter that couples to the first sleeve and rod insertion tool to control a depth of insertion of the rod insertion tool.

17. The method of claim 10, further comprising creating a passage using a trial rod prior to inserting the spinal stabilization rod.

18. The method of claim 10, further inserting the spinal stabilization rod through the channel in the side of the sleeve from outside of a surgical site.

19. A method for inserting a spinal stabilization rod comprising:

inserting an end portion of a spinal stabilization rod into a cavity of a rod retaining member of a rod insertion tool, wherein the rod insertion tool only engages the spinal stabilization rod at the end portion of the spinal stabilization rod, and wherein the rod insertion tool comprises:

an outer body defining a passage;

the rod retaining member, wherein the rod retaining member is coupled to the outer body and rotatable relative to the outer body;

a pivot rod disposed in the passage and translatable relative to the outer body;

a linkage coupled to an end portion of the pivot rod and the rod retaining member, wherein movement of the pivot rod in the passage causes the rod retaining member to rotate relative to the outer body;

a stopping feature adapted to allow the rod retaining member to at least partially fit in a channel in a side of a sleeve when the rod retaining member is in a first orientation and maintain the rod retaining member in a position relative to a collar of a bone fastener so that the end portion of the spinal stabilization rod extends past the collar when the rod retaining member is in a second orientation, wherein the stopping feature includes an extension that is wider than the channel;

securing the spinal stabilization rod to the rod retaining member external to a patient;

implanting the spinal stabilization rod into the patient percutaneously using the rod insertion tool to rotate the rod retaining member from the first orientation in which the spinal stabilization rod has a reduced profile to the second orientation.

20. The method of claim 19, wherein implanting the spinal stabilization rod percutaneously further comprises:

inserting the spinal stabilization rod into the patient in the first orientation through an incision through which a first sleeve coupled to a first bone anchor passes;

moving the spinal stabilization rod toward the first bone anchor;

rotating and moving the spinal stabilization rod using the rod insertion tool to pass under soft tissue between the first sleeve and a second sleeve; and wherein at least a portion of the rod insertion tool passes through a channel of the first sleeve during insertion.

* * * * *